(12) United States Patent
Summerton

(10) Patent No.: US 7,285,529 B2
(45) Date of Patent: *Oct. 23, 2007

(54) EMBEDDER COMPOSITIONS AND METHODS FOR DETECTING AND KILLING CELLS IN ACIDIC AREAS OF TUMORS

(75) Inventor: James Edward Summerton, Corvallis, OR (US)

(73) Assignee: Gene Tools, LLC, Philomath, OR (US)

( * ) Notice: Subject to any disclaimer, the term of this patent is extended or adjusted under 35 U.S.C. 154(b) by 197 days.

This patent is subject to a terminal disclaimer.

(21) Appl. No.: 11/069,849

(22) Filed: Feb. 28, 2005

(65) Prior Publication Data

US 2006/0193775 A1 Aug. 31, 2006

(51) Int. Cl.
*A01N 37/18* (2006.01)
(52) U.S. Cl. .......................................................... 514/2
(58) Field of Classification Search ..................... None
See application file for complete search history.

(56) References Cited

U.S. PATENT DOCUMENTS 6,030,941 A 2/2000 Summerton et al. ............ 514/2

OTHER PUBLICATIONS

Kozin, Shkarin, & Gerweck (2001) Cancer Research 61, 4740-4743.
(Kuin, Smets, Volk, Paans, Adams, Atema, Jahde, Maas, Rajewsky, & Visser (1994) Cancer Research 54, 3785-3792.
Bernard, Krenning, Breeman, Rolleman, Bakker, Visser, Macke, de Jong, Journal of Nuclear Medicine 38, 1929 (1997).
Garcia-Garayoa, Blauenstein, Bruehlmrier, Blanc, Iterbeke, Conrath, Tourwe & Schubiger (2002), The Journal of Nuclear Medicine 43, 374-383.
Prescott, Charles, Poulson, Page, Thrall, Vujaskovic, & Dewhirst (2000) Clinical Cancer Research 6, 2501-2505).
Jahde, Volk, Atema, Smets, Glusenkamp, Rajewsky (1992) Cancer Research 52, 6209-6215).

*Primary Examiner*—Anish Gupta
*Assistant Examiner*—Satyanarayana R. Gudibande
(74) *Attorney, Agent, or Firm*—Lori M. Friedman

(57) ABSTRACT

Embedder compositions effective for detecting or killing cells in acidic areas of tumors are described. Each composition includes an embedder peptide which at pH 7.2 and above is poly-anionic and so repels from cells in normal tissues, but at lower pH in hypoxic areas of tumors the embedder peptide converts to a non-ionic lipophilic form effective to embed into membranes of cells. Each composition also includes a cargo component which cannot be pulled across cell membranes by the embedder peptide and which is effective for detecting or killing cells in whose membranes the embedder peptide has embedded.

22 Claims, 22 Drawing Sheets

Comparative Figure 1a [RELATED ART]. Transporter mode of action
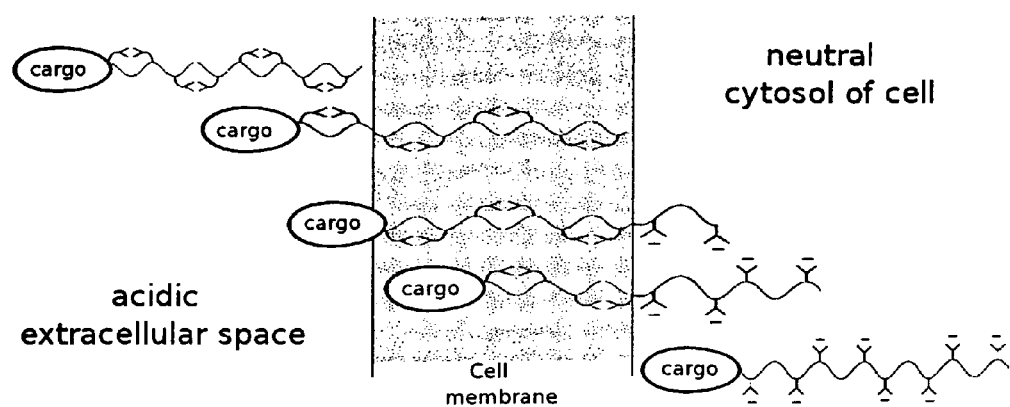
Figure 1. Embedder mode of action
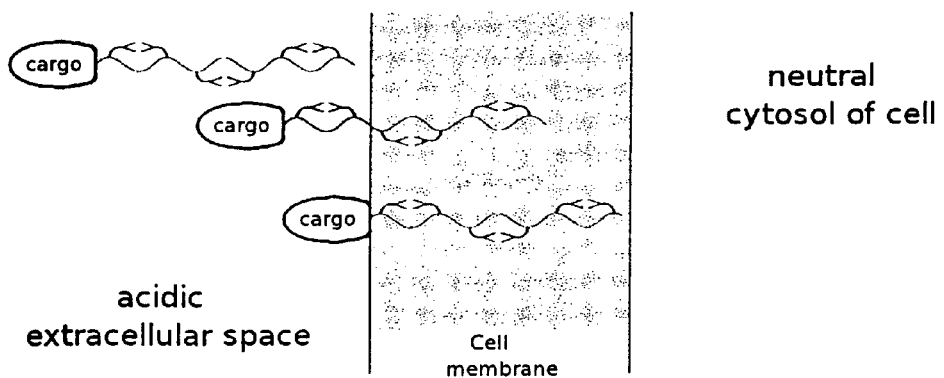

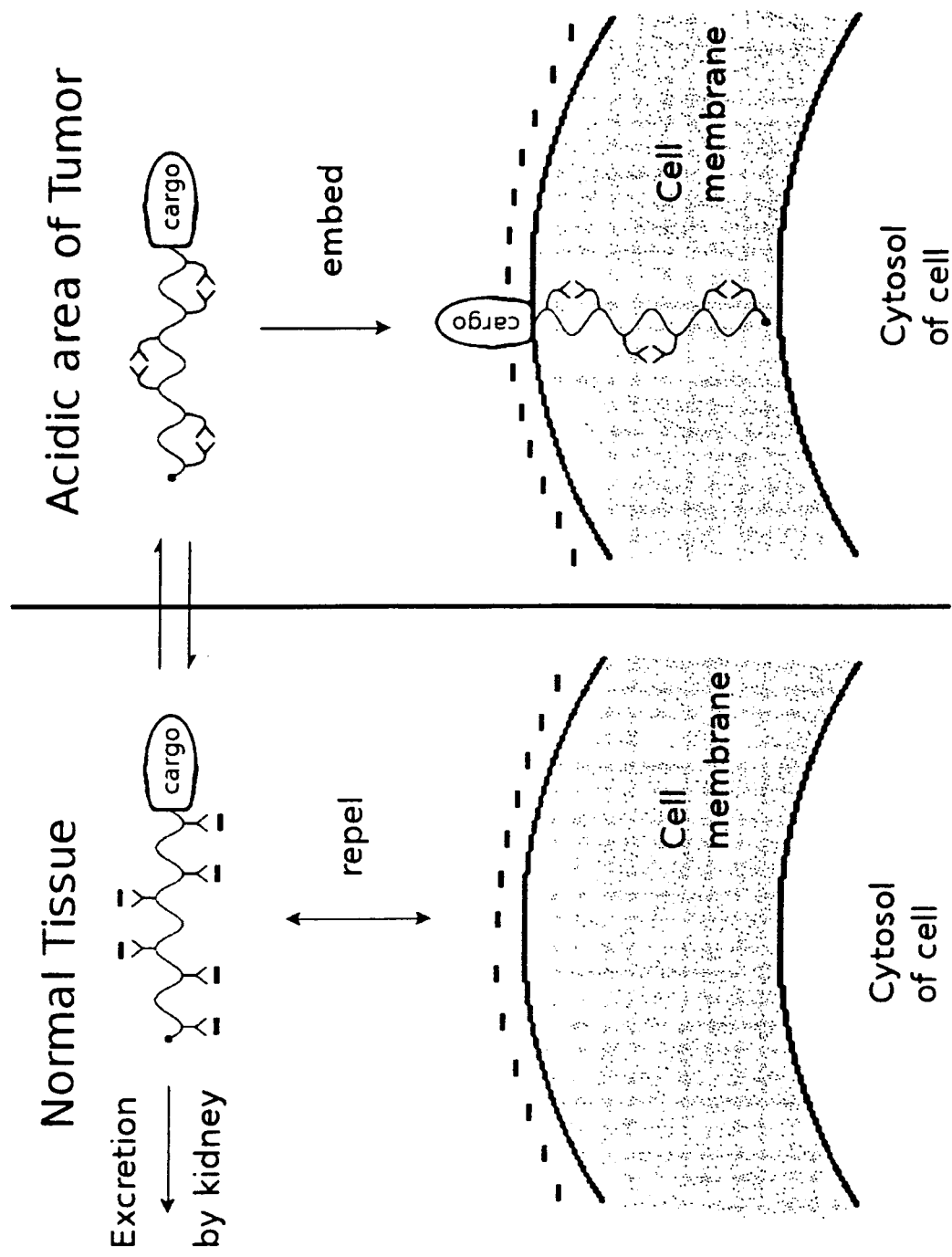
Figure 2. Embedder composition repelling from normal cell/embedding in tumor cell Figure 3. Dual-anchored embedder composition
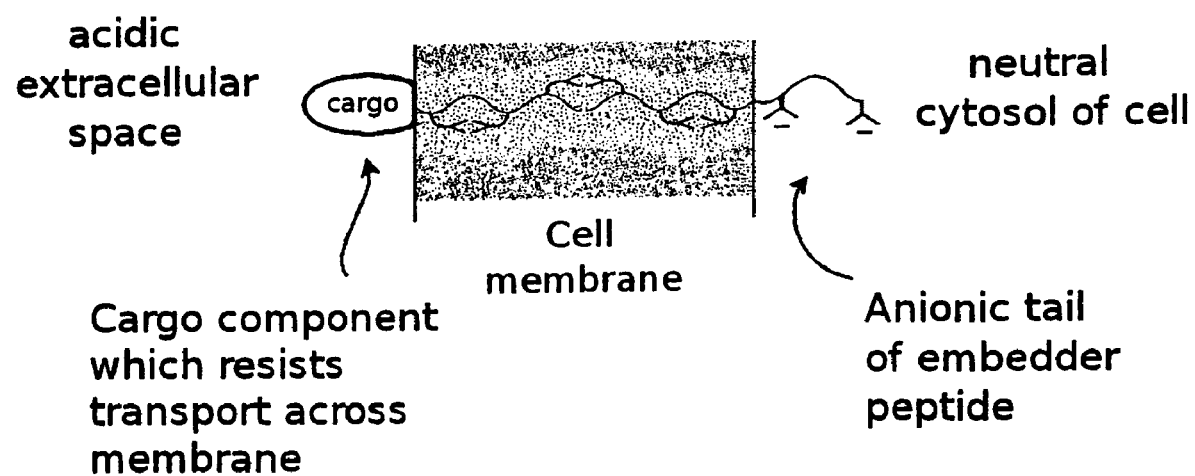

Figure 4. Double-hydrogen-bonded acid pair structure
a) Transition between anionic and lipophilic
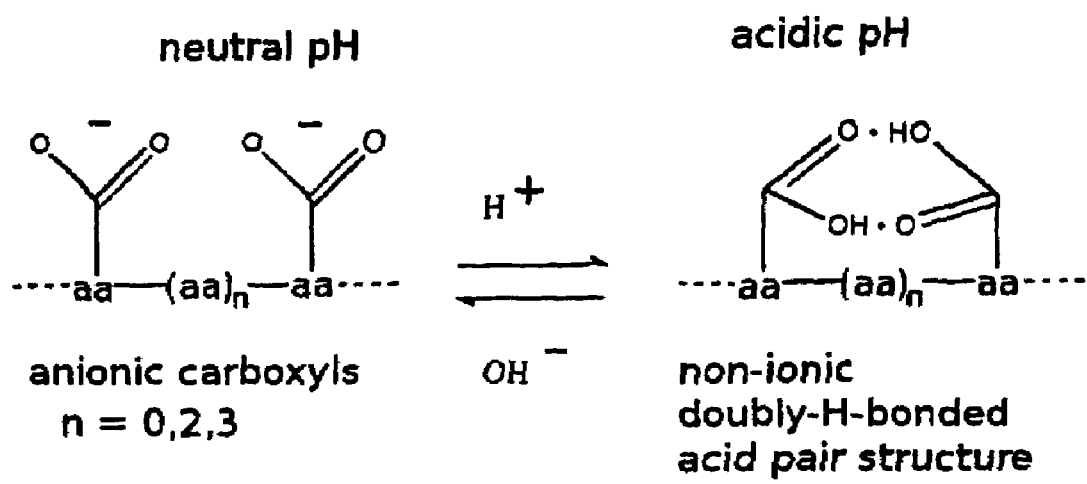
neutral pH
anionic carboxyls
n = 0,2,3
acidic pH
non-ionic
doubly-H-bonded
acid pair structure
b) Acid pair structure with 2 intervening amino acids
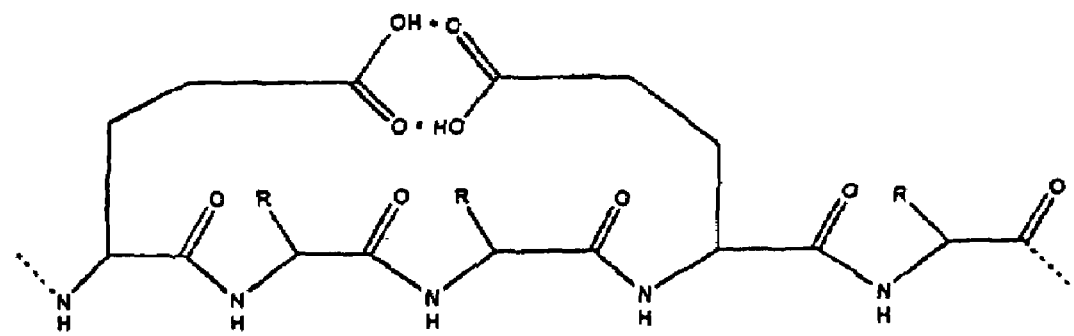

5. Axial distribution plots of acid pairs
a) Sequences with poor axial distribution/poor embedder activity
acid pairs
LLELLEELLEELLEELLEL
400° rotation
LLELLELLLELLELLLELLEL
700° rotation
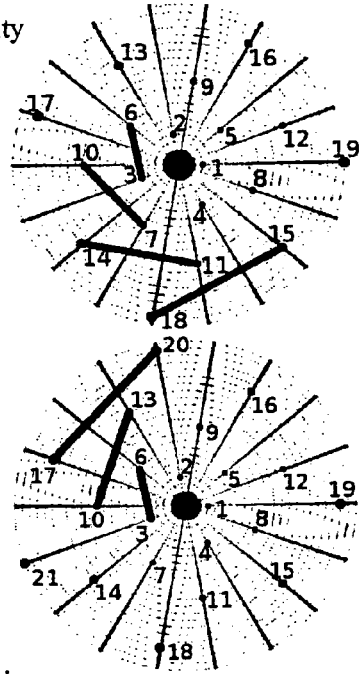
b) Sequences with good axial distribution/good embedder activity
LLELLLELELLELELLLELELLEA
550° rotation
LLELLLELELLLELELLLEL
600° rotation
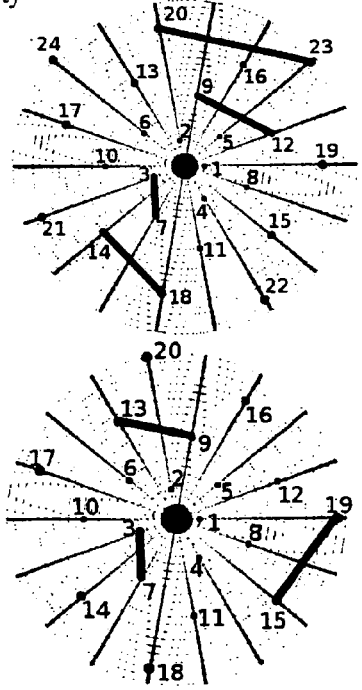

6. Key structural features for selecting transporter peptide sequences
   a) acid pair types

EE  acid pair with 0 intervening amino acids centerpoint of acid pair

ELLE  acid pair with two intervening amino acids centerpoint of acid pair  (L is a lipophilic amino acid)

ELLLE  acid pair with 3 intervening amino acids centerpoint of acid pair  (L is a lipophilic amino acid)

b) axial rotation values between adjacent acid pairs

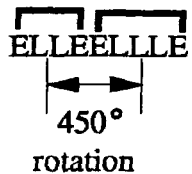
ELLEELLLE
450° rotation

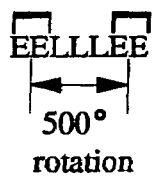
EELLLEE
500° rotation

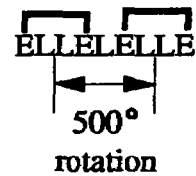
ELLELELLE
500° rotation

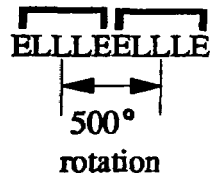
ELLLEELLLE
500° rotation

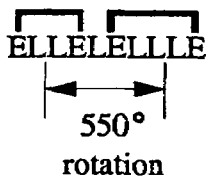
ELLELELLLE
550° rotation

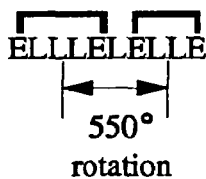
ELLLELELLE
550° rotation

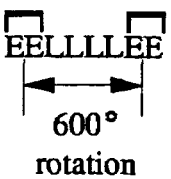
EELLLLEE
600° rotation

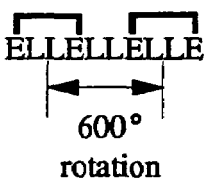
ELLELLELLE
600° rotation

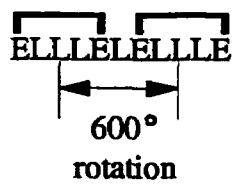
ELLLELELLLE
600° rotation

ELLLELLELLE
650°

7. Graphical selection of embedder sequences
a) 500° rotation values, EE acid pair type
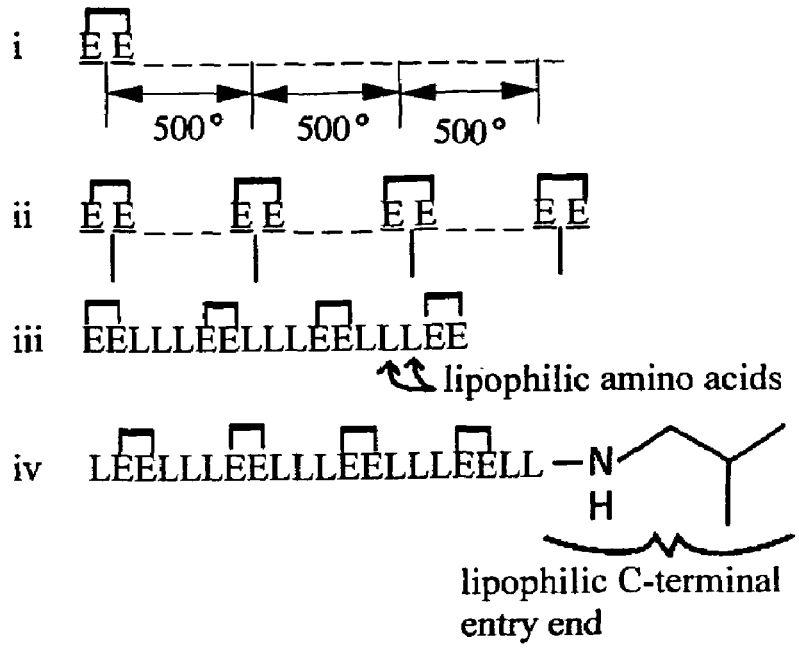
b) 550° rotation values, ELLE and ELLLE acid pair types
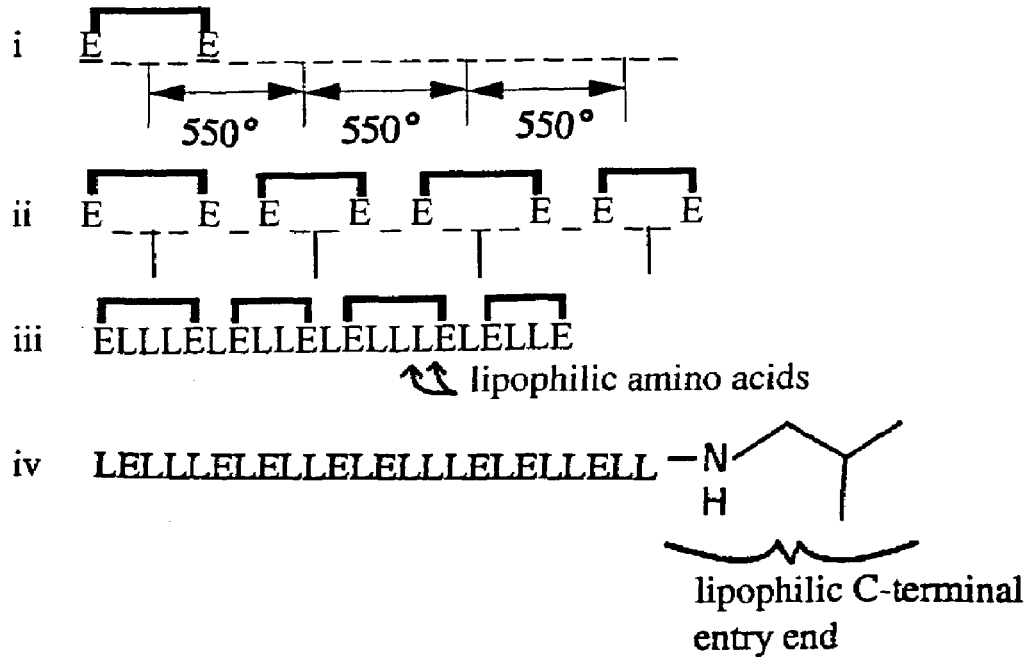

8. Embedder sequences, each with a single acid pair type
a) 500° axial rotation values
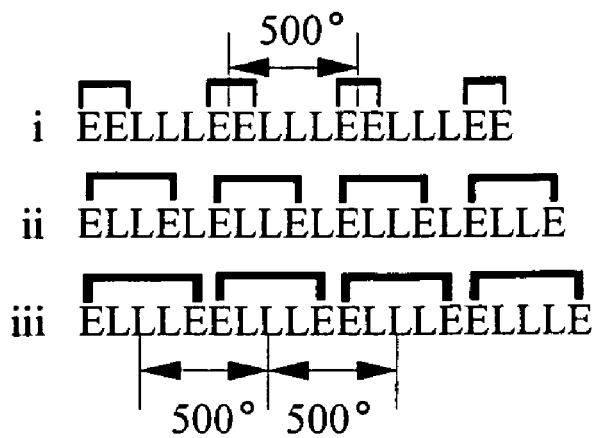
b) 550° axial rotation values
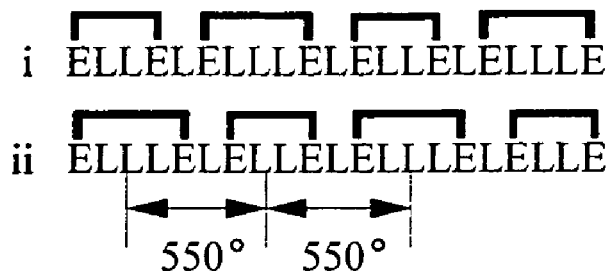
c) 600° axial rotation values
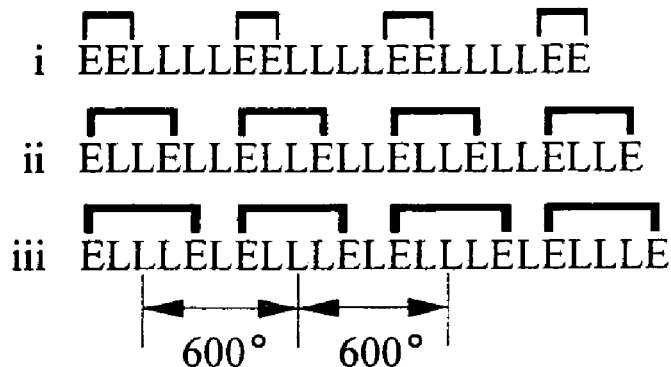

9. Embedder sequences with mixed rotation values
a) alternating 500° and 550° rotation values
 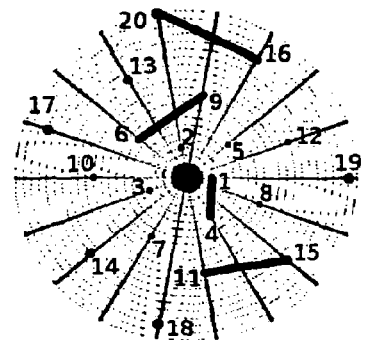
b) alternating 550° and 600° rotation values
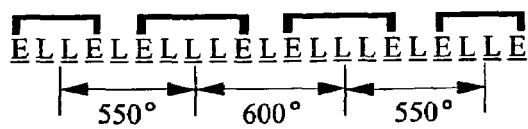 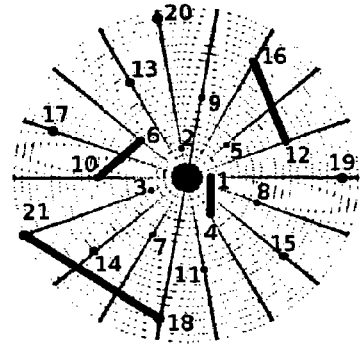
c) alternating 500° and 600° rotation values
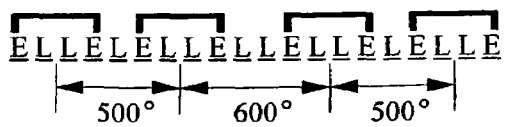 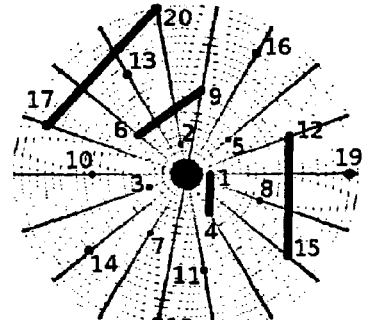
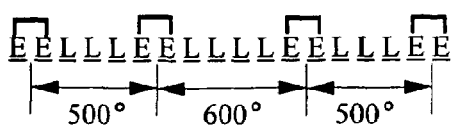 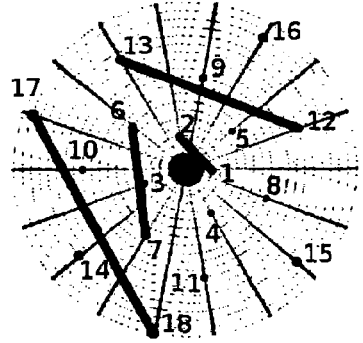

10. Embedder sequences with EE acid pairs
    mixed with ELLE and ELLLE acid pairs
a) EE acid pairs alternating with ELLE acid pairs
b) EE acid pairs alternating with ELLLE acid pairs
c) EE acid pairs with both ELLE and ELLLE acid pairs
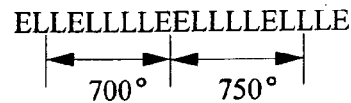
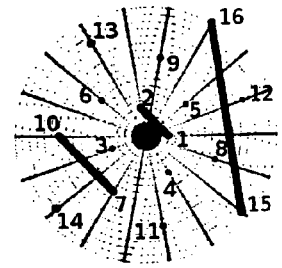
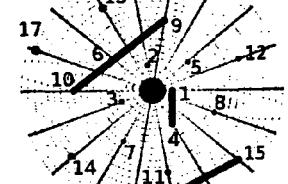
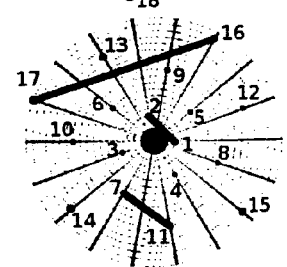
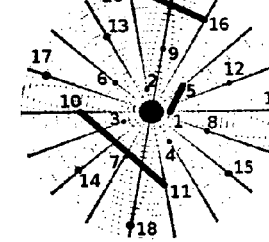
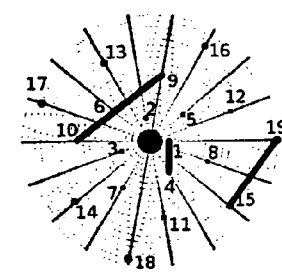

Figure 11. C-terminal entry end of embedder peptide
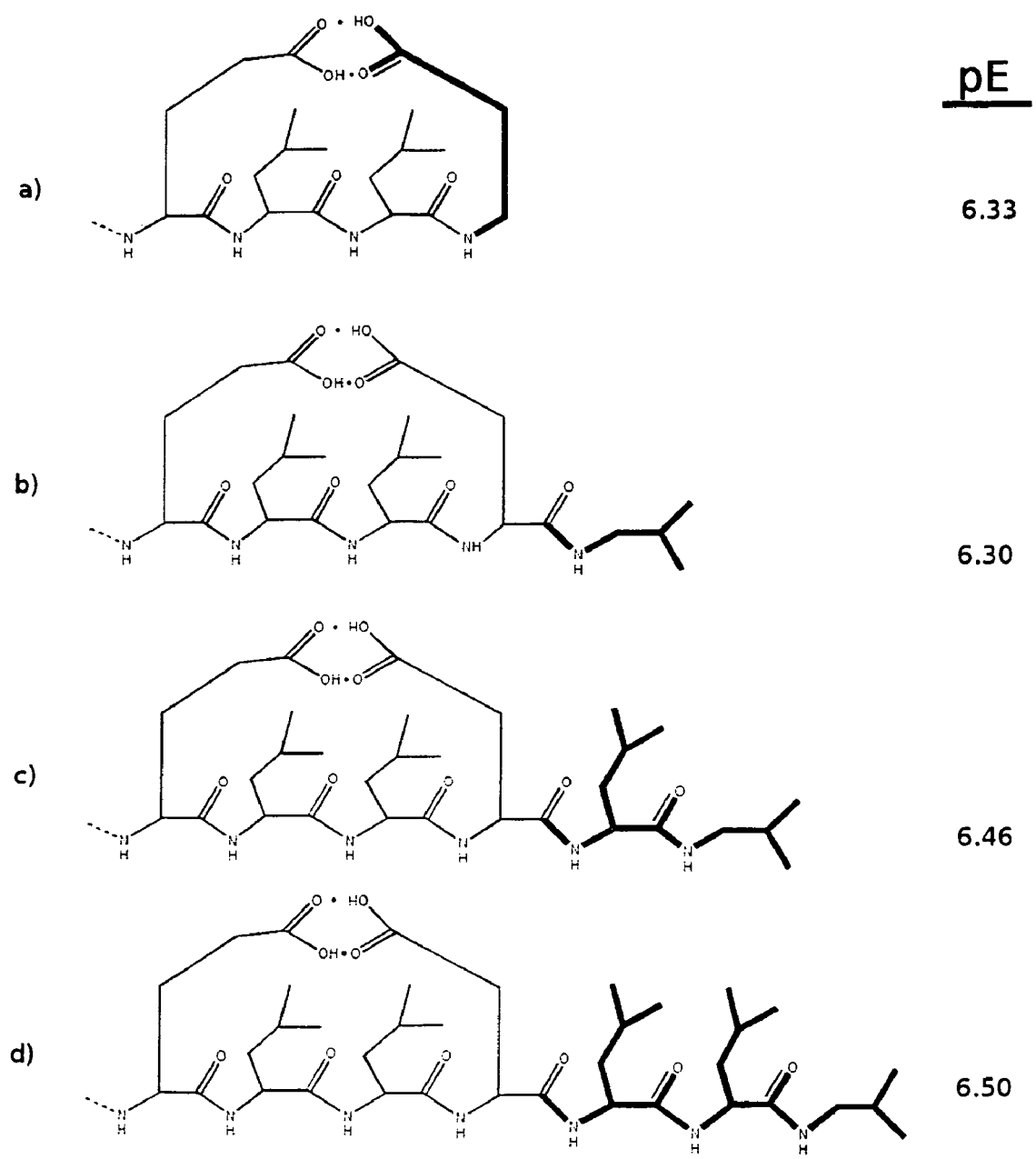

Figure 12. N-terminal entry end of embedder peptide
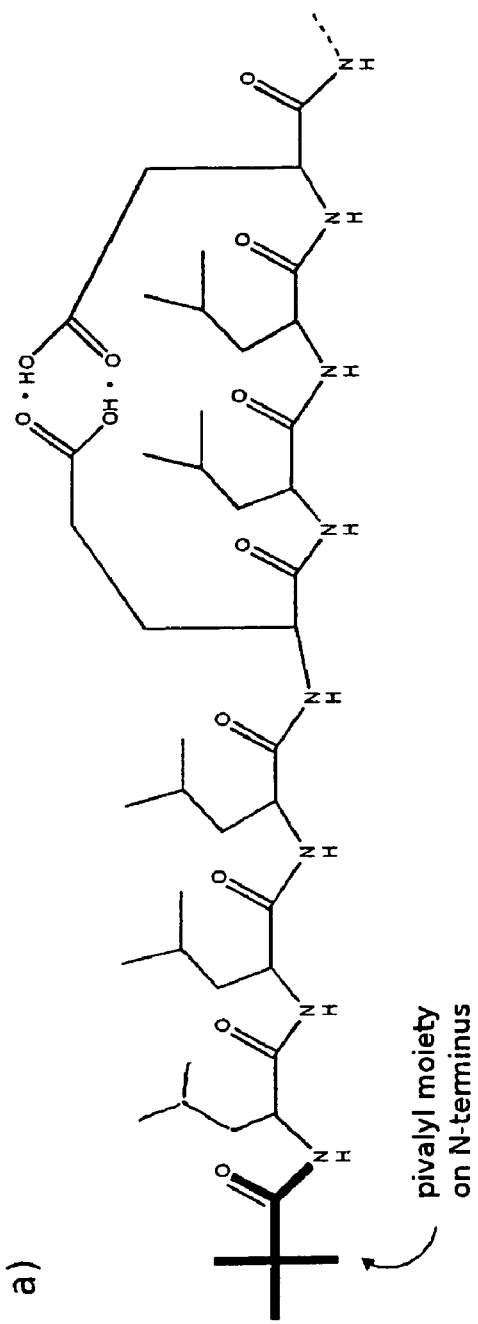
a) pivalyl moiety on N-terminus
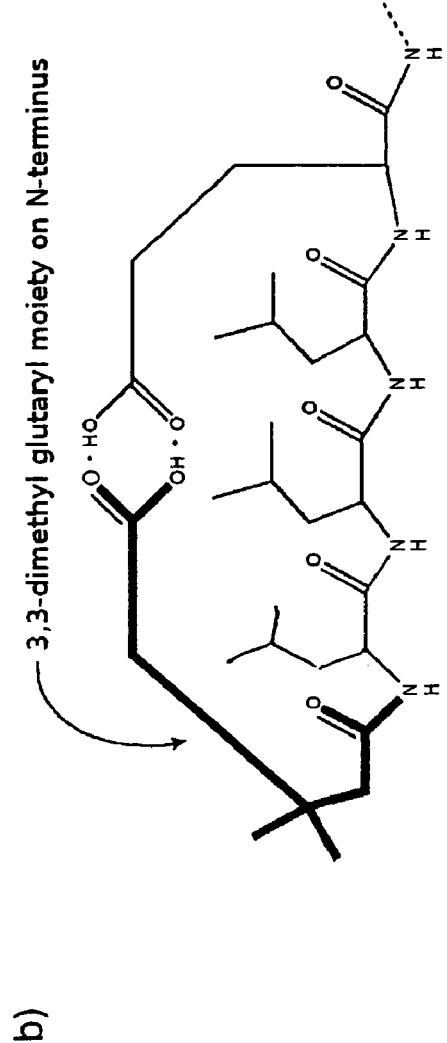
b) 3,3-dimethyl glutaryl moiety on N-terminus Figure 13. Representative embedder compositions

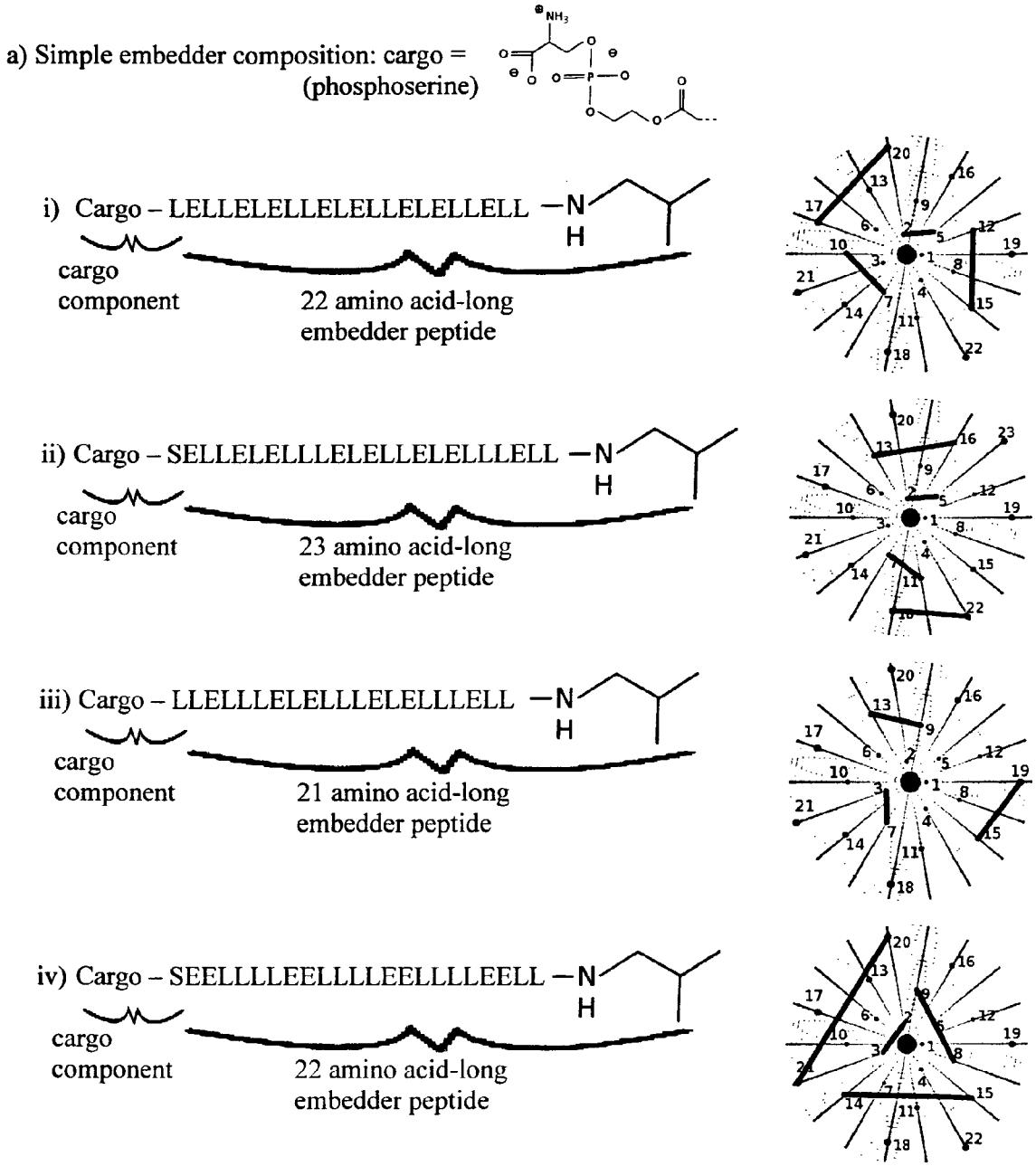

a) Simple embedder composition: cargo = (phosphoserine)

i) Cargo – LELLELELLELELLELELLELL —NH—
   cargo component | 22 amino acid-long embedder peptide ii) Cargo – SELLELELLLELELLELELLLELL —NH—
   cargo component | 23 amino acid-long embedder peptide iii) Cargo – LLELLLELELLLELELLLELL —NH—
   cargo component | 21 amino acid-long embedder peptide iv) Cargo – SEELLLLEELLLLEELLLLEELL —NH—
   cargo component | 22 amino acid-long embedder peptide

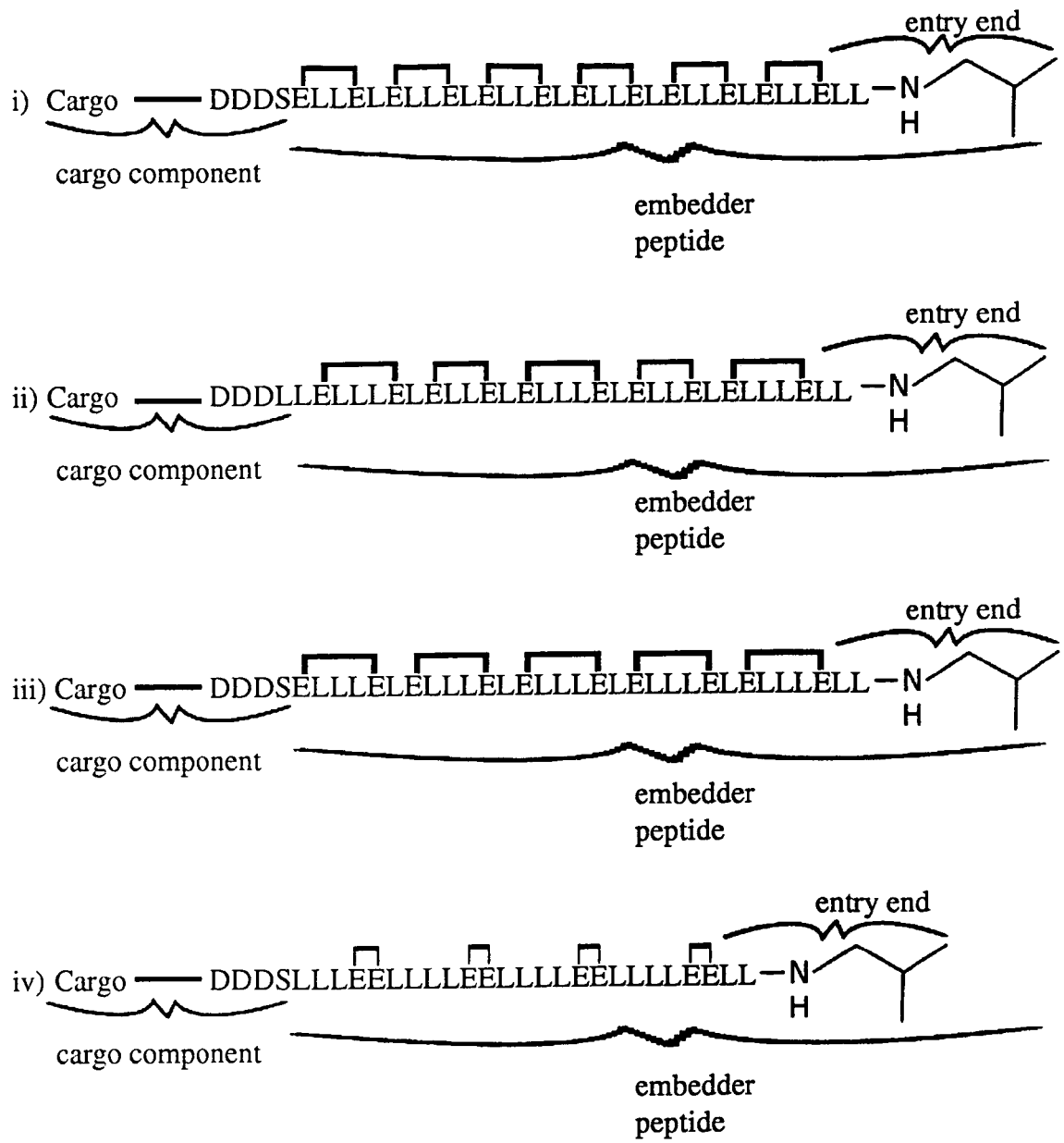
13b. Dual-anchor embedder compositions

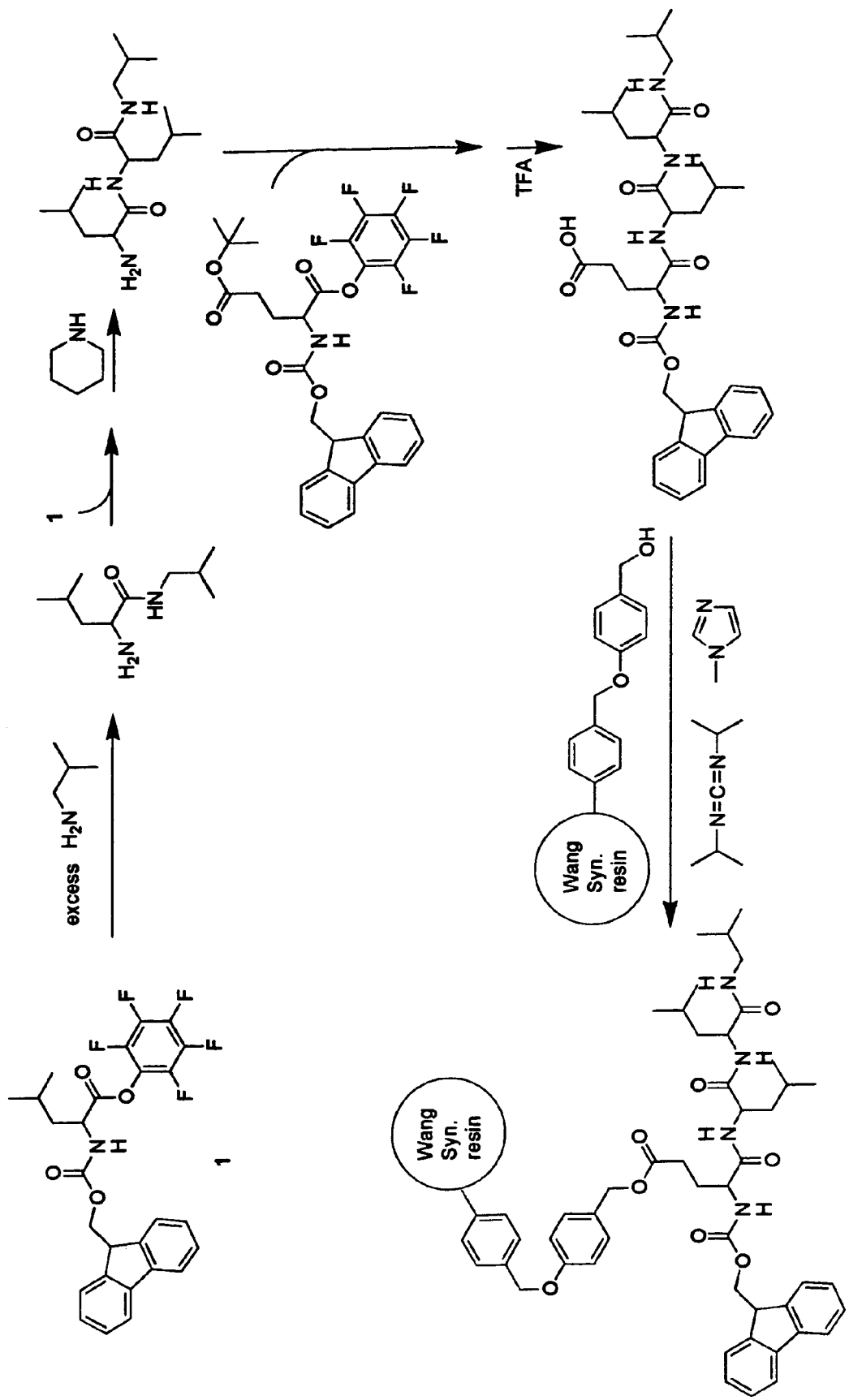
Figure 14. Preparation of Wang resin containing pre-formed C-terminal entry end

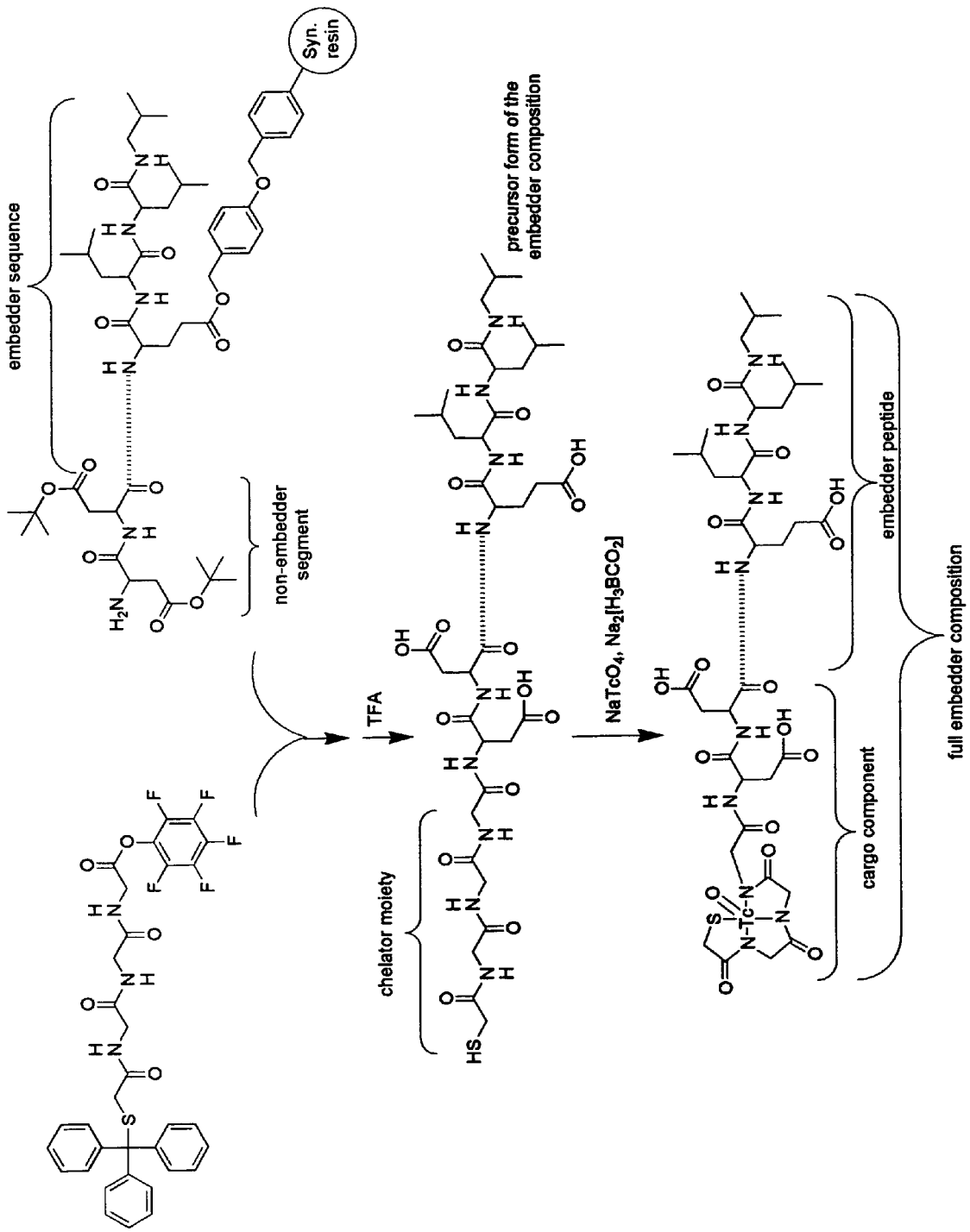
Figure 15a. Attachment of diagnostic cargo component to N-terminus of embedder peptide

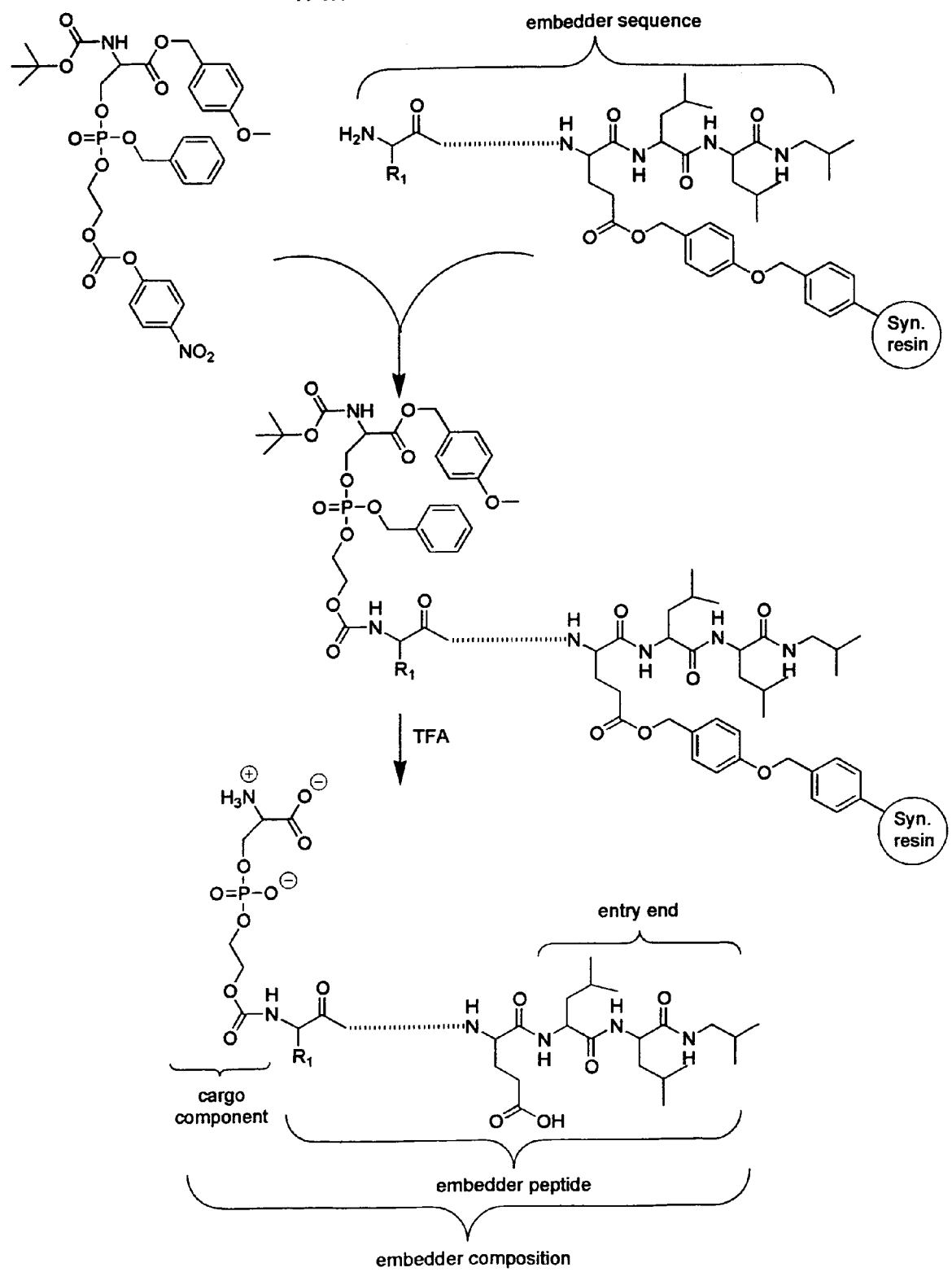
Figure 15b. Attachment of therapeutic cargo component to N-terminus of embedder peptide

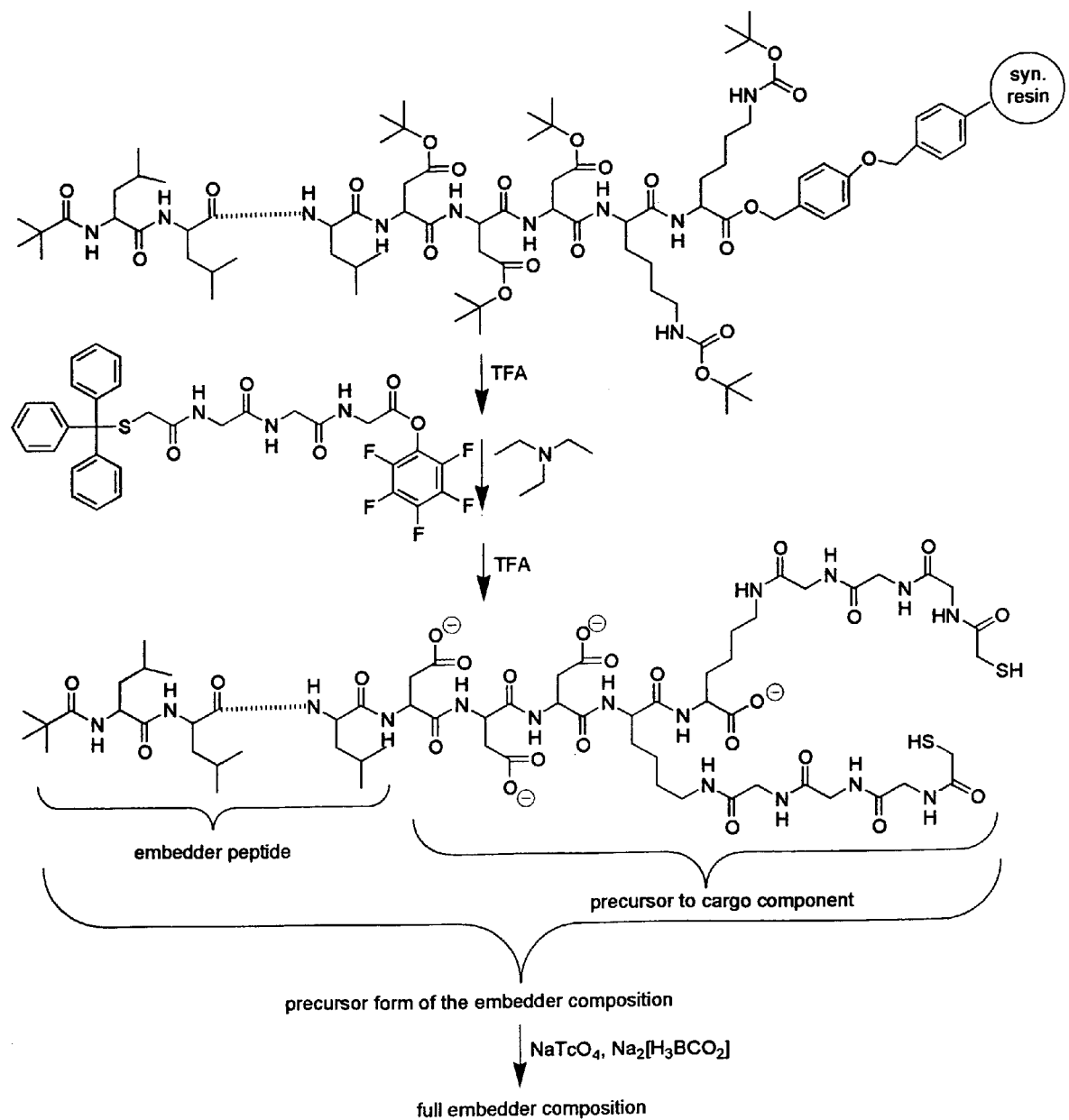
Figure 16a. Attachment of two diagnostic cargo moieties to C-terminus of embedder peptide

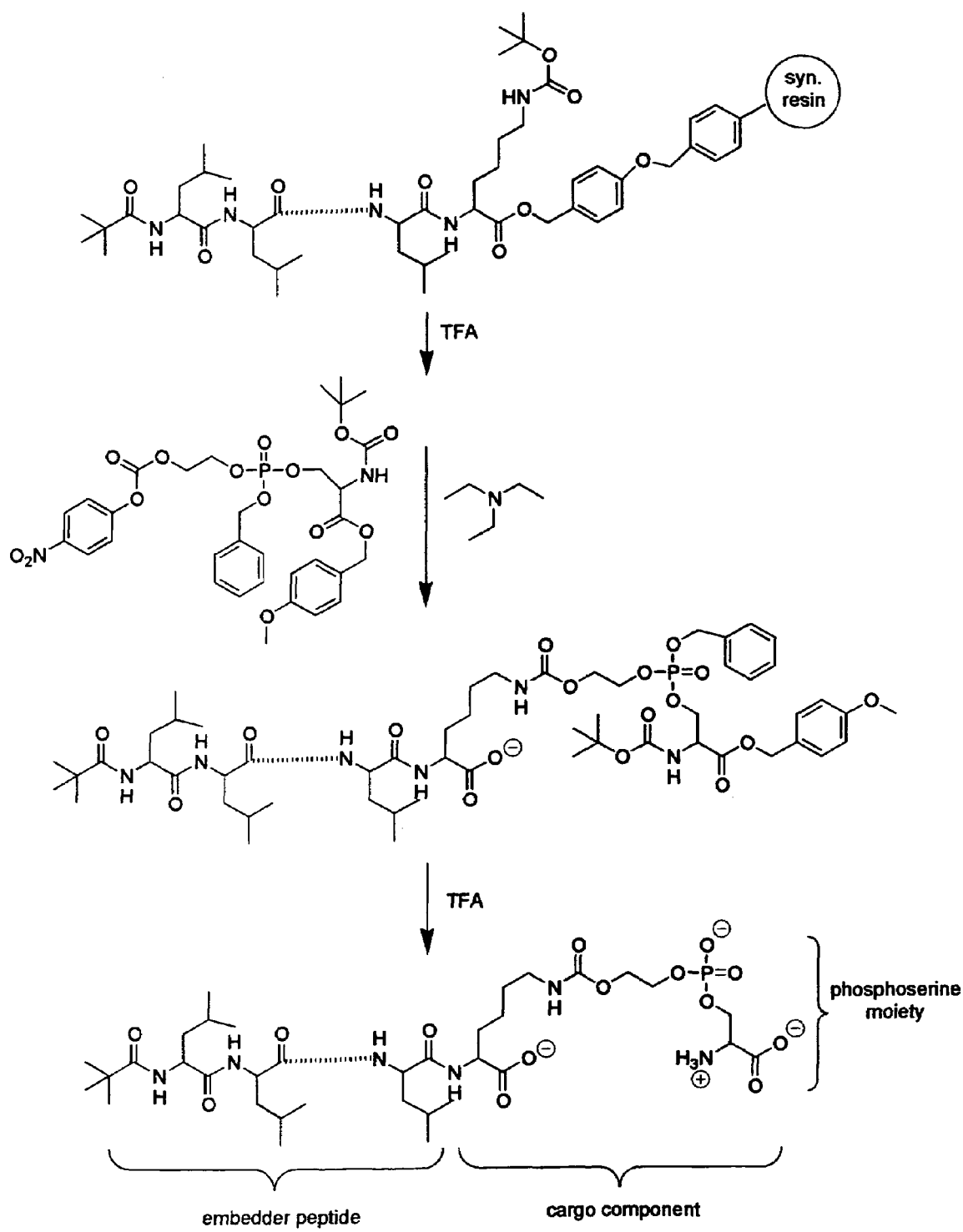
Figure 16b. Attachemnt of a therapeutic cargo to C-terminus of embedder peptide

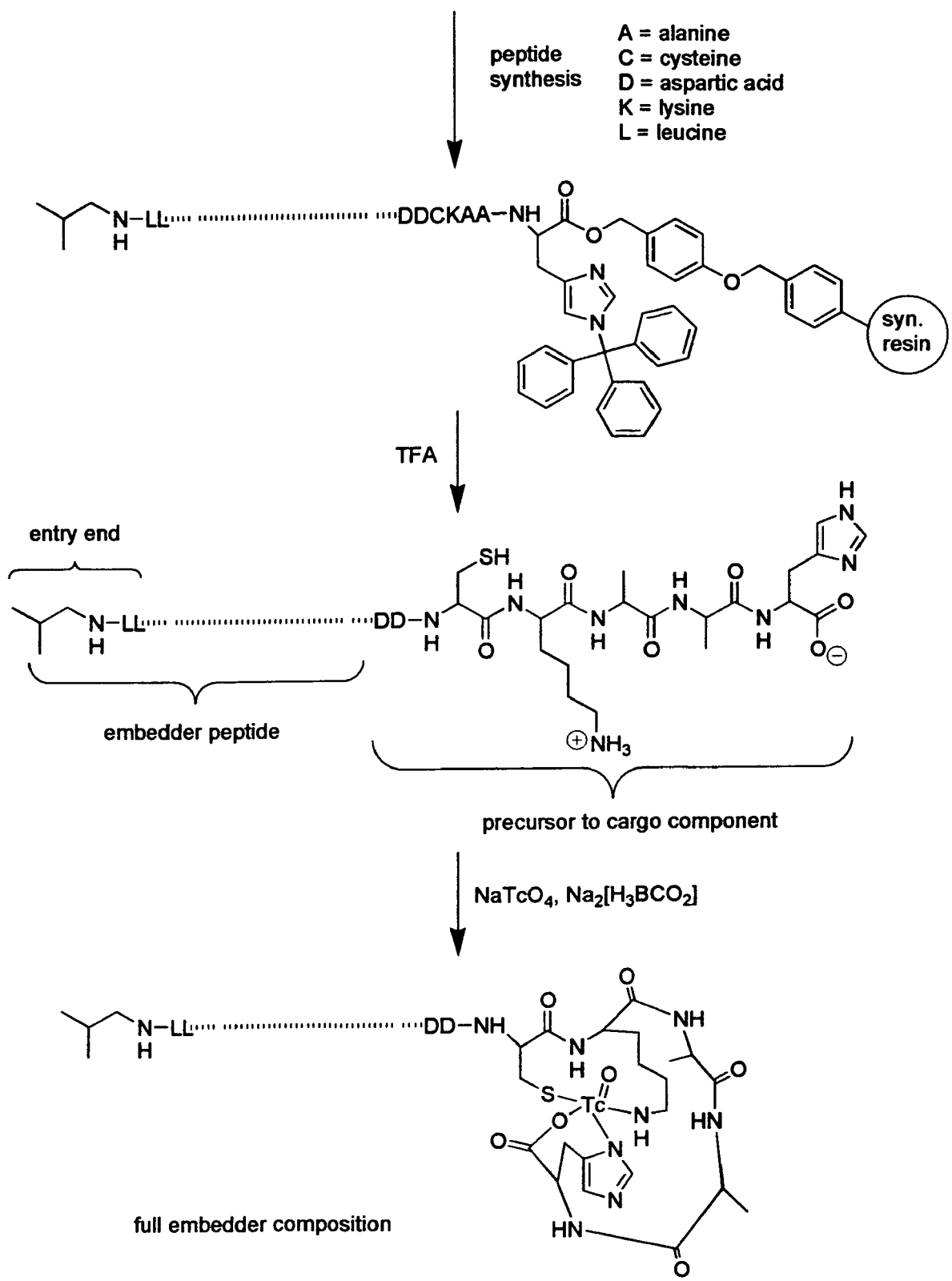
Figure 16c. Incorporation of a precursor to a cargo component during peptide synthesis

Figure 17. Representative embedder compositions for diagnostic application
a) Lower pE
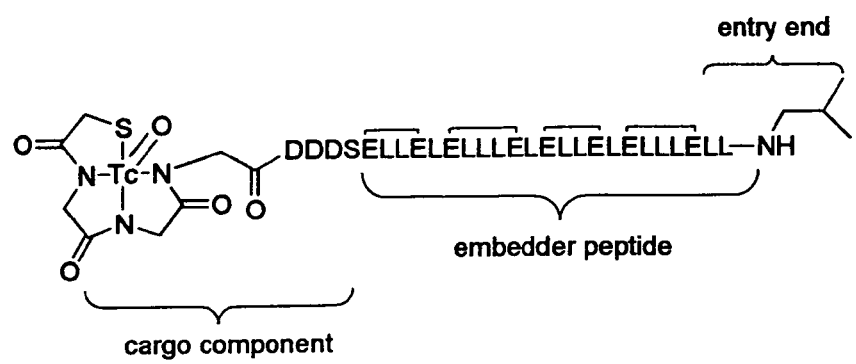
B) Higher pE
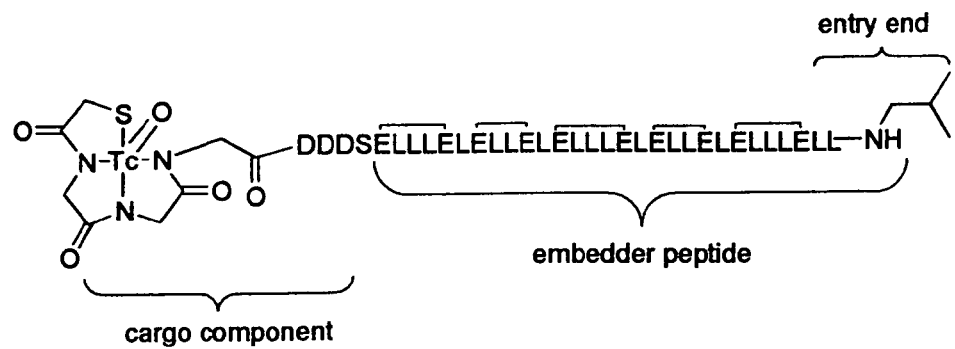

Figure 18. Representative embedder compositions for therapeutic application
a) Lower pE
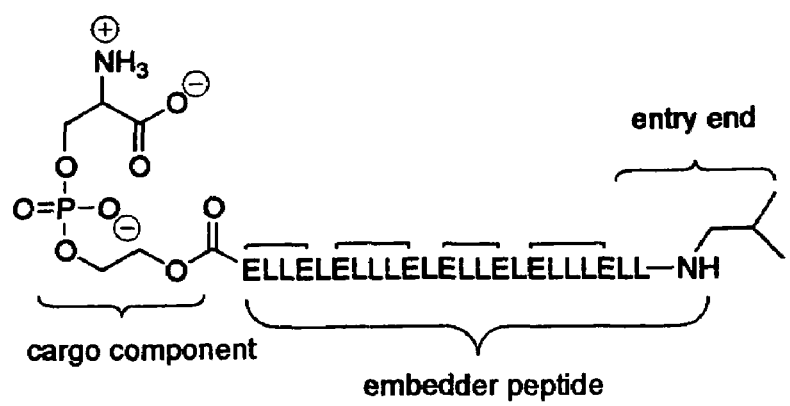
B) Higher pE
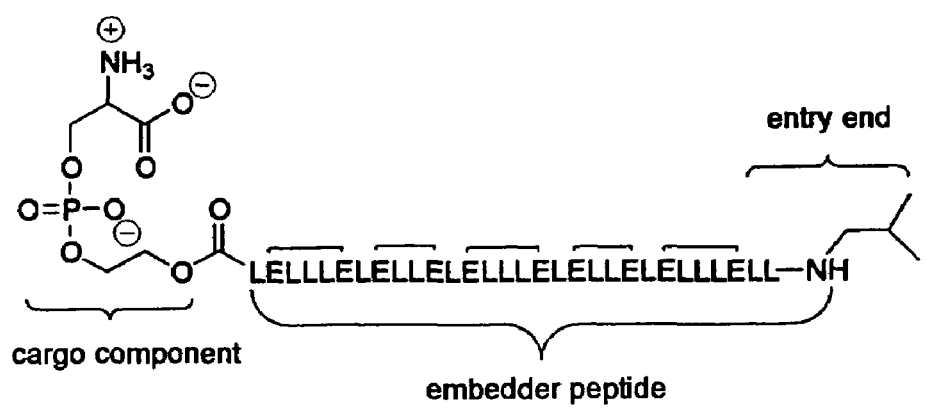

SEQUENCE LISTING

<160> NUMBER OF SEQ ID NOS: 47

<210> SEQ ID NO 1
<211> LENGTH: 16
<212> TYPE: PRT
<213> ORGANISM: human

<400> SEQUENCE: 1

Glu Leu Leu Glu Leu Glu Leu Leu Glu Leu Glu Leu Leu Glu Leu
1               5                   10                  15

<210> SEQ ID NO 2
<211> LENGTH: 16
<212> TYPE: PRT
<213> ORGANISM: human

<400> SEQUENCE: 2

Glu Leu Leu Leu Glu Leu Glu Leu Leu Glu Leu Glu Leu Leu Leu Glu
1               5                   10                  15

<210> SEQ ID NO 3
<211> LENGTH: 16
<212> TYPE: PRT
<213> ORGANISM: human

<400> SEQUENCE: 3

Glu Leu Leu Leu Glu Leu Glu Leu Leu Glu Leu Glu Leu Leu Leu Glu
1               5                   10                  15

<210> SEQ ID NO 4
<211> LENGTH: 16
<212> TYPE: PRT
<213> ORGANISM: human

<400> SEQUENCE: 4

Glu Leu Leu Glu Leu Glu Leu Leu Leu Glu Leu Glu Leu Leu Glu Leu
1               5                   10                  15

<210> SEQ ID NO 5
<211> LENGTH: 11
<212> TYPE: PRT
<213> ORGANISM: human

<400> SEQUENCE: 5

Glu Leu Leu Glu Leu Glu Leu Leu Leu Glu Leu
1               5                   10

<210> SEQ ID NO 6
<211> LENGTH: 11
<212> TYPE: PRT
<213> ORGANISM: human

<400> SEQUENCE: 6

Glu Leu Leu Leu Glu Leu Glu Leu Leu Glu Leu
1               5                   10

<210> SEQ ID NO 7
<211> LENGTH: 6
<212> TYPE: PRT
<213> ORGANISM: human

<400> SEQUENCE: 7

Glu Leu Leu Leu Glu Leu

-continued

```
1               5

<210> SEQ ID NO 8
<211> LENGTH: 16
<212> TYPE: PRT
<213> ORGANISM: human

<400> SEQUENCE: 8

Glu Leu Leu Leu Glu Leu Glu Leu Leu Glu Leu Glu Leu Leu Leu Glu
1               5                   10                  15

<210> SEQ ID NO 9
<211> LENGTH: 16
<212> TYPE: PRT
<213> ORGANISM: human

<400> SEQUENCE: 9

Glu Leu Leu Glu Leu Glu Leu Leu Glu Leu Glu Leu Leu Glu Leu
1               5                   10                  15

<210> SEQ ID NO 10
<211> LENGTH: 30
<212> TYPE: PRT
<213> ORGANISM: human

<400> SEQUENCE: 10

Leu Glu Leu Leu Leu Glu Leu Glu Leu Leu Glu Leu Glu Leu Leu Leu
1               5                   10                  15

Glu Leu Glu Leu Leu Glu Leu Glu Leu Glu Leu Leu Leu Glu
            20                  25                  30

<210> SEQ ID NO 11
<211> LENGTH: 19
<212> TYPE: PRT
<213> ORGANISM: human

<400> SEQUENCE: 11

Leu Leu Glu Leu Leu Glu Glu Leu Leu Glu Glu Leu Leu Glu Glu Leu
1               5                   10                  15

Leu Glu Leu

<210> SEQ ID NO 12
<211> LENGTH: 14
<212> TYPE: PRT
<213> ORGANISM: human

<400> SEQUENCE: 12

Leu Leu Leu Leu Leu Leu Leu Leu Leu Leu Leu Leu Leu Leu
1               5                   10

<210> SEQ ID NO 13
<211> LENGTH: 24
<212> TYPE: PRT
<213> ORGANISM: human

<400> SEQUENCE: 13

Leu Leu Glu Leu Leu Leu Glu Leu Glu Leu Leu Glu Leu Glu Leu Leu
1               5                   10                  15

Leu Glu Leu Glu Leu Leu Glu Ala
            20

<210> SEQ ID NO 14
<211> LENGTH: 20
```

```
<212> TYPE: PRT
<213> ORGANISM: human

<400> SEQUENCE: 14

Leu Leu Glu Leu Leu Leu Glu Leu Glu Leu Leu Leu Glu Leu Glu Leu
1               5                   10                  15
Leu Leu Glu Leu
            20

<210> SEQ ID NO 15
<211> LENGTH: 9
<212> TYPE: PRT
<213> ORGANISM: human

<400> SEQUENCE: 15

Glu Leu Leu Glu Glu Leu Leu Leu Glu
1               5

<210> SEQ ID NO 16
<211> LENGTH: 7
<212> TYPE: PRT
<213> ORGANISM: human

<400> SEQUENCE: 16

Glu Glu Leu Leu Leu Glu Glu
1               5

<210> SEQ ID NO 17
<211> LENGTH: 9
<212> TYPE: PRT
<213> ORGANISM: human

<400> SEQUENCE: 17

Glu Leu Leu Glu Leu Glu Leu Leu Glu
1               5

<210> SEQ ID NO 18
<211> LENGTH: 10
<212> TYPE: PRT
<213> ORGANISM: human

<400> SEQUENCE: 18

Glu Leu Leu Leu Glu Glu Leu Leu Leu Glu
1               5                   10

<210> SEQ ID NO 19
<211> LENGTH: 10
<212> TYPE: PRT
<213> ORGANISM: human

<400> SEQUENCE: 19

Glu Leu Leu Glu Leu Glu Leu Leu Leu Glu
1               5                   10

<210> SEQ ID NO 20
<211> LENGTH: 10
<212> TYPE: PRT
<213> ORGANISM: human

<400> SEQUENCE: 20

Glu Leu Leu Leu Glu Leu Glu Leu Leu Glu
1               5                   10

<210> SEQ ID NO 21
```

```
<211> LENGTH: 8
<212> TYPE: PRT
<213> ORGANISM: human

<400> SEQUENCE: 21

Glu Glu Leu Leu Leu Leu Glu Glu
1               5

<210> SEQ ID NO 22
<211> LENGTH: 10
<212> TYPE: PRT
<213> ORGANISM: human

<400> SEQUENCE: 22

Glu Leu Leu Glu Leu Leu Glu Leu Leu Glu
1               5                   10

<210> SEQ ID NO 23
<211> LENGTH: 11
<212> TYPE: PRT
<213> ORGANISM: human

<400> SEQUENCE: 23

Glu Leu Leu Leu Glu Leu Glu Leu Leu Glu
1               5                   10

<210> SEQ ID NO 24
<211> LENGTH: 11
<212> TYPE: PRT
<213> ORGANISM: human

<400> SEQUENCE: 24

Glu Leu Leu Leu Glu Leu Leu Glu Leu Leu Glu
1               5                   10

<210> SEQ ID NO 25
<211> LENGTH: 24
<212> TYPE: PRT
<213> ORGANISM: human

<400> SEQUENCE: 25

Glu Leu Leu Leu Glu Glu Leu Glu Leu Glu Leu Leu Glu Leu Glu Leu
1               5                   10                  15

Leu Leu Glu Leu Glu Leu Leu Glu
            20

<210> SEQ ID NO 26
<211> LENGTH: 24
<212> TYPE: PRT
<213> ORGANISM: human

<400> SEQUENCE: 26

Leu Glu Leu Leu Leu Glu Leu Glu Leu Leu Glu Leu Glu Leu Leu Leu
1               5                   10                  15

Glu Leu Glu Leu Leu Glu Leu Leu
            20

<210> SEQ ID NO 27
<211> LENGTH: 23
<212> TYPE: PRT
<213> ORGANISM: human

<400> SEQUENCE: 27

Glu Leu Leu Leu Glu Leu Glu Leu Leu Leu Glu Leu Glu Leu Leu Leu
```

```
                1               5                  10                 15
Glu Leu Glu Leu Leu Leu Glu
            20

<210> SEQ ID NO 28
<211> LENGTH: 32
<212> TYPE: PRT
<213> ORGANISM: human

<400> SEQUENCE: 28

Leu Glu Leu Leu Leu Glu Leu Glu Leu Leu Glu Leu Glu Leu Leu
1               5                  10                 15

Leu Glu Leu Glu Leu Leu Leu Glu Leu Glu Leu Leu Leu Glu Leu Leu
            20                  25                 30

<210> SEQ ID NO 29
<211> LENGTH: 22
<212> TYPE: PRT
<213> ORGANISM: human

<400> SEQUENCE: 29

Glu Leu Leu Glu Leu Glu Leu Glu Leu Leu Glu Leu Glu Leu Leu Glu
1               5                  10                 15

Leu Glu Leu Leu Leu Glu
            20

<210> SEQ ID NO 30
<211> LENGTH: 21
<212> TYPE: PRT
<213> ORGANISM: human

<400> SEQUENCE: 30

Glu Leu Leu Leu Glu Leu Glu Leu Leu Glu Leu Glu Leu Leu Leu Glu
1               5                  10                 15

Leu Glu Leu Leu Glu
            20

<210> SEQ ID NO 31
<211> LENGTH: 20
<212> TYPE: PRT
<213> ORGANISM: human

<400> SEQUENCE: 31

Glu Glu Leu Leu Leu Leu Glu Glu Leu Leu Leu Leu Glu Glu Leu Leu
1               5                  10                 15

Leu Leu Glu Glu
            20

<210> SEQ ID NO 32
<211> LENGTH: 22
<212> TYPE: PRT
<213> ORGANISM: human

<400> SEQUENCE: 32

Glu Leu Leu Glu Leu Leu Glu Leu Leu Glu Leu Leu Glu Leu Leu Glu
1               5                  10                 15

Leu Leu Glu Leu Leu Glu
            20

<210> SEQ ID NO 33
<211> LENGTH: 23
<212> TYPE: PRT
```

<213> ORGANISM: human

<400> SEQUENCE: 33

Glu Leu Leu Leu Glu Leu Glu Leu Leu Leu Glu Leu Glu Leu Leu Leu
1               5                   10                  15

Glu Leu Glu Leu Leu Leu Glu
            20

<210> SEQ ID NO 34
<211> LENGTH: 20
<212> TYPE: PRT
<213> ORGANISM: human

<400> SEQUENCE: 34

Glu Leu Leu Glu Leu Glu Leu Leu Glu Leu Glu Leu Leu Leu Glu Glu
1               5                   10                  15

Leu Leu Leu Glu
            20

<210> SEQ ID NO 35
<211> LENGTH: 21
<212> TYPE: PRT
<213> ORGANISM: human

<400> SEQUENCE: 35

Glu Leu Leu Glu Leu Glu Leu Leu Leu Glu Leu Glu Leu Leu Leu Glu
1               5                   10                  15

Leu Glu Leu Leu Glu
            20

<210> SEQ ID NO 36
<211> LENGTH: 20
<212> TYPE: PRT
<213> ORGANISM: human

<400> SEQUENCE: 36

Glu Leu Leu Glu Leu Glu Leu Leu Glu Leu Leu Glu Leu Leu Glu Leu
1               5                   10                  15

Glu Leu Leu Glu
            20

<210> SEQ ID NO 37
<211> LENGTH: 18
<212> TYPE: PRT
<213> ORGANISM: human

<400> SEQUENCE: 37

Glu Glu Leu Leu Leu Glu Glu Leu Leu Leu Leu Glu Glu Leu Leu Leu
1               5                   10                  15

Glu Glu

<210> SEQ ID NO 38
<211> LENGTH: 16
<212> TYPE: PRT
<213> ORGANISM: human

<400> SEQUENCE: 38

Glu Glu Leu Leu Leu Leu Glu Leu Leu Glu Leu Leu Leu Leu Glu Glu
1               5                   10                  15

<210> SEQ ID NO 39
<211> LENGTH: 18

<212> TYPE: PRT
<213> ORGANISM: human

<400> SEQUENCE: 39

Glu Leu Leu Glu Leu Leu Leu Glu Glu Leu Leu Leu Leu Glu Leu
1               5                   10                  15

Leu Glu

<210> SEQ ID NO 40
<211> LENGTH: 17
<212> TYPE: PRT
<213> ORGANISM: human

<400> SEQUENCE: 40

Glu Glu Leu Leu Leu Leu Glu Leu Leu Leu Glu Leu Leu Leu Glu
1               5                   10                  15

Glu

<210> SEQ ID NO 41
<211> LENGTH: 20
<212> TYPE: PRT
<213> ORGANISM: human

<400> SEQUENCE: 41

Glu Leu Leu Leu Glu Leu Leu Leu Leu Glu Glu Leu Leu Leu Glu
1               5                   10                  15

Leu Leu Leu Glu
            20

<210> SEQ ID NO 42
<211> LENGTH: 19
<212> TYPE: PRT
<213> ORGANISM: human

<400> SEQUENCE: 42

Glu Leu Leu Glu Leu Leu Leu Glu Glu Leu Leu Leu Leu Glu Leu
1               5                   10                  15

Leu Leu Glu

<210> SEQ ID NO 43
<211> LENGTH: 28
<212> TYPE: PRT
<213> ORGANISM: human

<400> SEQUENCE: 43

Leu Glu Leu Leu Glu Leu Glu Leu Leu Glu Leu Glu Leu Leu Leu Glu
1               5                   10                  15

Glu Leu Leu Leu Glu Leu Glu Leu Glu Leu Leu
            20                  25

<210> SEQ ID NO 44
<211> LENGTH: 30
<212> TYPE: PRT
<213> ORGANISM: human

<400> SEQUENCE: 44

Leu Glu Leu Leu Leu Glu Leu Glu Leu Leu Glu Leu Glu Leu Leu
1               5                   10                  15

Glu Leu Glu Leu Leu Glu Leu Glu Leu Leu Leu Glu Leu Leu
            20                  25                  30

```
<210> SEQ ID NO 45
<211> LENGTH: 32
<212> TYPE: PRT
<213> ORGANISM: human

<400> SEQUENCE: 45

Leu Glu Leu Leu Leu Glu Leu Glu Leu Leu Leu Glu Leu Glu Leu Leu
1               5                   10                  15

Leu Glu Leu Glu Leu Leu Leu Glu Leu Glu Leu Leu Leu Glu Leu Leu
                20                  25                  30

<210> SEQ ID NO 46
<211> LENGTH: 29
<212> TYPE: PRT
<213> ORGANISM: human

<400> SEQUENCE: 46

Leu Glu Leu Leu Glu Leu Glu Leu Leu Glu Leu Glu Leu Leu Leu Glu
1               5                   10                  15

Leu Glu Leu Leu Glu Leu Glu Leu Leu Leu Glu Leu Leu
                20                  25

<210> SEQ ID NO 47
<211> LENGTH: 35
<212> TYPE: PRT
<213> ORGANISM: human

<400> SEQUENCE: 47

Leu Glu Leu Leu Glu Leu Glu Leu Leu Leu Glu Leu Glu Leu Leu Glu
1               5                   10                  15

Leu Glu Leu Leu Leu Glu Leu Glu Leu Leu Glu Leu Glu Leu Leu Leu
                20                  25                  30

Glu Leu Leu
35
```

US 7,285,529 B2

EMBEDDER COMPOSITIONS AND METHODS FOR DETECTING AND KILLING CELLS IN ACIDIC AREAS OF TUMORS

RELATED PATENT APPLICATION

The present application is filed concurrently with an application No. 11/069,387 entitled: "Improved Transporter Compositions and Methods for Detecting and Killing Cells in Acidic Areas of Tumors", filed in 28 Feb. 2005, invented by applicant and likewise assigned to GENE TOOLS, LLC.

FIELD OF THE INVENTION

The present invention relates to the use of embedder compositions for detecting or killing cells in acidic areas of tumors. At the neutral pH of normal tissues the embedder peptide of the composition of this invention exists in a poly-anionic form effective to repel from and not embed into membranes of cells. In acidic areas of tumors the embedder peptide converts to a non-ionic lipophilic form effective to embed into cell membranes and position a cargo component on the cell surface.

BACKGROUND AND RELATED ART

Tumors larger than microscopic size have inadequate and abnormal vasculature. As a consequence, areas of tumors that are more than a few tens of microns from a capillary are generally hypoxic. Cells in such hypoxic areas of tumors either die or convert to anaerobic metabolism which results in their excreting lactic acid. Because of the poor circulation in tumors, that excreted lactic acid builds up in the interstitial space in hypoxic areas of tumors.

There are two important consequences of this process.

1) While the pH in the interstitial space in normal tissues ranges from about 7.2 to 7.5, the interstitial space in hypoxic areas of tumors is acidic, with pH ranging from as low as about 6.0 in areas most distant from capillaries, up to about 7.0 closer to capillaries.

2) While tumor cells in close proximity to capillaries are characterized by high metabolic rates and fast cell division, the tumor cells in acidic areas more distant from capillaries have lower metabolic rates and are slower-dividing or non-dividing. The slow-dividing and non-dividing tumor cells are referred to as quiescent.

Conventional cancer therapies, including chemotherapy and radiation, are generally fairly effective in killing fast-dividing cells, but because conventional cancer therapies are explicitly selected on the basis of their ability to spare slow-dividing and non-dividing cells typical of most normal tissues, said cancer therapies are also relatively ineffective against slow-dividing and non-dividing quiescent tumor cells. As a consequence, cancer treatments typically kill predominantly the fast-dividing cells of a tumor, while sparing the quiescent cells of the tumor. The initial killing of the fast-dividing tumor cells causes the tumor to go into remission. After those killed cells have been disposed of by the body's normal cleanup processes, all too often the treatment-resistant quiescent cancer cells in the hypoxic areas of the tumor slowly regain access to adequate oxygen, nutrients, and waste disposal, thus allowing them to revert to high metabolic rate and fast cell division. Reversion of the previously-quiescent cancer cells manifests as the dreaded relapse that so often kills cancer patients.

To achieve more effective treatment of tumors it is desirable to have a means for sensitive detection of quiescent cancer cells in virtually all tumors. Also desired is to have a broadly effective means for selectively killing those treatment-resistant quiescent cancer cells without concomitant killing of cells in normal tissues.

RELATED ART

There are two distinct types of compositions for detecting and treating cells in acidic areas of tumors: transporter compositions and embedder compositions. Compositions of the transporter type carry their cargos into the cytosol of cells, as illustrated in Comparative FIG. 1a [RELATED ART]. In contrast, compositions of the embedder type of the instant invention position their cargos on the outer surface of cells, as illustrated in FIG. 1.

Related art transporter compositions are described in: a) U.S. Pat. No. 6,030,941, issued in 1997 to applicant et al and assigned to AVI BioPharma, Inc.; and in b) a co-submitted and co-pending patent application by applicant titled: "Improved Transporter Compositions And Methods For Detecting And Killing Cells In Acidic Areas Of Tumors". These related art transporter compositions repel from cells at the pH in normal tissues, but transport into the cytosol of cells in acidic areas of tumors. Such transporter compositions contain cargos which can be pulled across cell membranes by the attached transporter peptide. Cargos of transporter compositions must be relatively small and lipophilic so they can be pulled across the cell membrane by the attached transporter peptide, and for therapeutic application said cargos must be effective to kill the cell when said cargo is positioned within that cell. Examples of such cargos for transporter compositions are a variety of intracellular toxins which have been isolated from bacteria, plants, and animals. In contrast, cargos of embedder compositions of the instant invention can be relatively large and polar since they need not pass through a membrane, and for therapeutic application said cargos can be designed to exploit some component of the body's natural extracellular cell-killing machinery, such as phagocytic cells or the innate immune system.

SUMMARY OF THE INVENTION

To address the problem of selectively detecting and treating quiescent cancer cells in hypoxic areas of tumors, applicant has devised embedder compositions which are designed to repel from cells in normal tissues, but to embed into the membranes of cells in a broad range of acidic areas of tumors. As illustrated in FIG. 2, when these embedder compositions are introduced into the body, if a tumor larger than microscopic size is present, a portion of the introduced dose will embed into the membranes of cells in acidic areas of the tumor, with the remainder of the introduced dose being rapidly excreted from the body. When the embedder composition is to be used for detecting tumors, it includes a cargo component suitable for detecting the embedded composition. When the embedder composition is to be used for treating the quiescent cells of tumors it includes a cargo component effective for killing the cells in whose membranes the composition has embedded.

The embedder composition of this invention includes two key components: an embedder peptide which repels from cells at neutral pH, but embeds into membranes of cells in acidic areas of tumors; and, a cargo component which prevents passage across cell membranes, and which is effective for detecting or killing cells into whose membranes the embedder composition has embedded.

In one aspect of the invention, an embedder composition provides a means for delivering a cargo onto the surface of cells in acidic areas of tumors, without concomitant delivery onto cell surfaces in areas of normal pH elsewhere in the body. This selectivity is achieved by use of an embedder peptide sequence which contains properly positioned carboxylic acid pairs interspersed with lipophilic amino acids.

The invention further includes a diagnostic method consisting of introducing one or more embedder compositions into a patient, particularly a human patient, for the purpose of detecting any tumors which are present and which have acidic areas. Typically about 1 to about 24 hours after introducing the embedder composition (to allow clearance of non-embedded composition from the body) the patient is scanned to detect the presence and position of any embedder composition embedded into membranes of cells in acidic areas of tumors. For such applications the embedder composition includes a cargo which can be readily detected by methods known and practiced in the medical diagnostics art. Cargos for this purpose include fluors, radioisotopes, contrast agents, and the like.

The invention further includes an enhanced diagnostic method which additionally entails introducing into the patient a substance, such as glucose, which is effective to temporarily further reduce the pH in hypoxic areas of tumors.

The diagnostic method of the present invention also includes methods for minimizing re-uptake of transporter composition by the kidneys. These methods include treating the patient with a substance to minimize endocytotic uptake of peptides in the proximal tubules, and treating the patient with a substance to temporarily render the urine slightly alkaline.

In another aspect, the invention includes a therapeutic method consisting of introducing one or more embedder compositions into a patient, and particularly a human patient, for the purpose of killing cells in acidic areas of any tumors which are present. For such applications, the embedder composition includes a cargo which can kill cells, either directly or indirectly. Cargos for this purpose include such agents as radioisotopes, and other direct-acting cell-killing agents known in the cancer therapy art. Cargos may also be substances which work indirectly, such as a phosphoserine moiety, which, when positioned on the outer surface of the plasma membrane of a tumor cell, serves as a signal for engulfment and destruction of that cell by a macrophage. Cargos also include other indirect-acting cell-killing agents known in the cancer therapy art.

The therapeutic method of the invention, for killing quiescent cancer cells in acidic areas of tumors, is preferably carried out in combination with conventional radiation or chemotherapy known in the art, for the purpose of also killing the fast-dividing cells of tumors.

The present invention further includes an enhanced therapeutic method which additionally entails introducing into the patient a substance, such as glucose, which is effective to temporarily further reduce the pH in hypoxic areas of tumors.

The therapeutic method of the invention also includes methods for minimizing re-uptake of embedder composition by the kidneys. These methods include treating the patient with a substance to minimize endocytotic uptake of peptides in the proximal tubules, and treating the patient with a substance to temporarily render the urine slightly alkaline.

BRIEF DESCRIPTION OF THE FIGURES

FIG. 1 illustrates the embedder mode of action by embedder compositions of the instant invention.

Comparative FIG. 1a (RELATED ART) illustrates the transporter mode of action by transporter compositions described in applicant's co-pending patent application.

FIG. 2 illustrates an embedder composition repelling from a normal cell and embedding into the membrane of a tumor cell.

FIG. 3 illustrates the positioning of a dual-anchored embedder composition across a cell membrane.

FIG. 4 depicts a double-hydrogen-bonded acid pair structure.

FIG. 5 shows axial distribution plots of acid pairs.

FIG. 6 shows key structural features for selecting embedder peptide sequences.

FIG. 7 demonstrates the graphical selection of embedder peptide sequences.

FIG. 8 shows embedder peptide sequences, each with a single acid pair type.

FIG. 9 shows embedder peptide sequences with mixed axial rotation values

FIG. 10 shows embedder peptide sequences with EE acid pairs mixed with ELLE and ELLLE acid pairs.

FIG. 11 shows C-terminal entry ends of embedder peptides.

FIG. 12 shows N-terminal entry ends of embedder peptides.

FIG. 13 shows representative embedder compositions.

FIG. 14 depicts the preparation of Wang resin containing a pre-formed C-terminal entry end.

FIG. 15 depicts attachment of cargo components to N-terminus of embedder peptide.

FIG. 16 depicts attachment of cargo components to C-terminus of embedder peptide.

FIG. 17 shows representative embedder compositions for diagnostic application.

FIG. 18 shows representative embedder compositions for therapeutic application.

DEFINITIONS USED IN THIS INVENTION

The terms used herein have the following specific meanings, unless otherwise noted.

"Transporter" composition means a composition which includes both: a) a transporter peptide that is poly-anionic at neutral pH, but converts to a non-ionic lipophilic form in acidic areas of a tumor, and which is effective to transport a cargo into the cytosol of a cell; and, b) a cargo component.

"Embedder composition" means a composition which includes both: a) an embedder peptide which repels from cells at neutral pH, but embeds in cell membranes in acidic areas of tumors; and, b) a cargo component which prevents passage across cell membranes and which is effective for detecting or killing cells in whose membranes the embedder peptide is embedded.

"Precursor form of the embedder composition" means a composition which includes both: a) an embedder peptide which repels from cells at neutral pH, but embeds in cell membranes in acidic areas of tumors; and, b) a precursor to a cargo component, where said precursor is reactive toward a substance such that when said precursor and said substance are contacted they form a cargo component which prevents passage across cell membranes and which is effective for detecting or killing cells in whose membranes the embedder peptide is embedded.

"Embedder peptide" means an embedder peptide sequence, with a lipophilic entry end, which is polyanionic at the pH in normal tissues, but converts to a predominantly non-ionic lipophilic form effective to embed into cell membranes in acidic areas of tumors.

"Embedder sequence" means the amino acid sequence of the embedder peptide. Amino acid sequences presented herein follow the standard convention of the N-terminal amino acid starting on the left and the C-terminal amino acid ending on the right.

"Amino acid sequence motif" means a specific short amino acid sequence which comprises a portion of a complete embedder peptide. Two novel amino acid sequence motifs which are particularly preferred as segments of embedder peptides are: . . . ELLELELLLELELLEL . . . and . . . ELLLELELLELELLLE . . . .

"Acid pair" means a pair of side chain carboxylic acids in a peptide sequence, where there are zero, two, or three amino acids intervening in the peptide backbone between the side chains of the pair, and which under acidic conditions the carboxyls of the acid pair form a double-hydrogen-bonded carboxylic acid pair structure when the peptide is in an alpha helical confirmation as illustrated in FIG. 4.

"Lipophilic amino acid" (also designated as "L") means lipophilic amino acids, at least 90% of which are selected from the group consisting of: leucine, isoleucine, norleucine and methionine.

"L" means a lipophilic amino acid.

"Entry end" means the structural modifications at one terminus of the embedder peptide which, at a pH present or achievable in acidic areas of tumors, serve to dispose of the terminal ionic moiety typical of peptides, and render that peptide end sufficiently lipophilic to embed into cell membranes.

"pH of transition" (pT) means the pH at which half of the embedder peptides are in the buffer phase and half are in the octanol phase in the partitioning assay described in Example 5.

"pH of embedding" (pE) means the pH at which half of the embedder peptides have embedded into cell membranes in the membrane binding assay described in Example 6.

"Cargo component" means a substance which prevents passage across cell membranes because it is too large and/or polar to be pulled across cell membranes by the embedder peptide, and which is effective for detecting or killing the cell in whose membrane the embedder peptide has embedded. The cargo component includes at least one cargo, and may also include additional structure effective to prevent passage of the cargo through cell membranes, and/or effective to attach multiple cargos to a single embedder peptide, and/or effective to distance the cargo from the outer surface of the cell membrane in which the embedder peptide is embedded.

"Cargo" means a substance effective for detecting or for directly or indirectly killing the cells in whose membranes the embedder peptide is embedded.

"Diagnostic moiety" means a cargo effective for detecting the cells in whose membranes the embedder peptide is embedded.

"Therapeutic moiety" means a cargo effective for directly or indirectly killing the cells in whose membranes the embedder peptide is embedded.

"Non-embedder segment" means a portion of the cargo component comprising a sequence of generally polar amino acids joined to the embedder peptide at the end distal to the entry end, where said non-embedder segment may serve to prevent passage of the cargo through the cell membrane into the cytosol, and/or may serve for attachment of multiple cargos to a single embedder peptide, and/or may serve to distance the cargo from the cell membrane in which the embedder peptide is embedded.

"Tumor" means a cancerous mass which contains hypoxic/acidic areas. "Tumor", as used herein is also commonly referred to as a malignancy, or as a neoplasm, or as a malignant neoplasm, or as a solid cancer.

DETAILED DESCRIPTION OF PREFERRED EMBODIMENTS

I. Structure and Function of Embedder Composition

The embedder composition of the instant invention includes both an embedder peptide and a cargo component. The embedder peptide has an amino acid composition and sequence and a lipophilic entry end such that at about pH 7.2 and above the embedder peptide is poly-anionic, soluble in aqueous solution, and repels from negatively charged cell surfaces. At a lower pH present in acidic areas of tumors, ranging from about pH 6.0 to about 7.0, the embedder peptide converts to a largely non-ionic lipophilic form which is effective to embed into cell membranes. The cargo component prevents passage across cell membranes and includes one or more cargo moieties which are effective for detecting or for directly or indirectly killing cells into which the embedder peptide is embedded.

When these embedder compositions are introduced into the body, if a tumor larger than microscopic size is present, a portion of the introduced dose will embed into the membranes of cells in acidic areas of the tumor, with the remainder of the dose being excreted from the body, as illustrated in FIG. 2. When the composition is to be used for detecting tumors, it includes a cargo component effective for detecting the cells in whose membranes the embedder peptide is embedded. When the composition is to be used for treating tumors, it includes a cargo component effective for directly or indirectly killing the cells in whose membranes the embedder peptide is embedded.

A. Embedder Peptide of Embedder Composition

1. Design Challenges for Embedder Peptide

A key requirement in designing an embedder composition effective for detection or treatment of cells in acidic areas of tumors is to assure that the embedder peptide of said composition will carry a sufficient number of negative charges at the pH present in normal tissues (about pH 7.2 and above) to assure adequate aqueous solubility and repulsion from the anionic surface of cell membranes. Then at a pH present in hypoxic areas of tumors, typically in the range of about pH 6.0 to about 7.0, the embedder peptide must convert to a predominantly non-ionic lipophilic form effective to embed into the membrane of a cell. In typical peptides such transitions between anionic and non-ionic forms, mediated primarily by carboxylic acid side chains of glutamic and aspartic acids, are fairly broad, generally with 80% of the transition occurring over 1.0 pH unit, and said transitions generally occur in a pH range centered around pH 4.5. The challenges that must be met in designing an effective embedder peptide are:

a) to change the center point of the transition between anionic and non-ionic forms from around pH 4.5 in typical peptides up to about pH 6.2 to 6.9 for the embedder peptide, and preferably to about 6.5 to about 6.9;

b) to make that transition substantially sharper than in typical peptides, preferably sharpening that transition so that about 80% of the transition occurs within a range of less than about 0.5 pH unit; and, c) to render the non-ionic free acid form of the carboxylic acid moieties considerably less polar than is typical in nearly all peptides and proteins.

2. Length of Embedder Peptide

Experimental work carried out in support of this invention shows that the embedder peptide should be at least about 16 amino acids in length in order to be effective for embedding into the membranes of cells in acidic areas of tumors. However, longer embedder peptides whose length approaches the thickness of the lipophilic interior of the plasma membrane of cells (about 30 to 36 angstroms) appear to afford improved embedder properties. This 30 to 36 angstrom length corresponds to peptide sequences of 20 to 24 amino acids. In this context, experimental findings show that the pH at which embedder peptides of suitable sequence convert between their poly-anionic hydrophilic form and their non-ionic lipophilic form increases with increasing length, and the resistance of the membrane-embedded peptide to leaching out from the membrane is also expected to increase with increasing length of the embedder component. As a consequence, in comparison to shorter embedder peptides, the longer embedder peptides effectively embed in a greater range of hypoxic areas in tumors, and, once embedded, the longer embedder peptides should be more resistant to leaching out from the tumor cell membranes and subsequent excretion from the body.

Still longer embedder peptides, substantially longer than 24 amino acids, can afford an additional advantage by serving to strongly anchor the cargo on the outer surface of the cell in acidic regions of the tumor by virtue of ionization of a portion of the embedder peptide within the cytosol of the cell, as illustrated in FIG. 3. Such dual anchoring, on the extracellular side of the membrane by the cargo component, and on the cytosolic side of the membrane by the ionized tail of the embedder peptide, can be particularly valuable in cases where the embedding occurs while the pH within the tumor is temporarily reduced, such as by addition of glucose. In such cases, even when the pH within the tumor returns after several hours to its original higher pH, the cargo can remain firmly anchored on the outer surface of the cell due to the ionized tail of the embedder peptide within the cytosol of the cell. In this context, it is noteworthy that P-31 NMR studies indicate that the pH within the cytosol of cancer cells in acidic areas of tumors is generally in the range of about 7.2 to about 7.4—even though the pH in the surrounding extracellular medium can be as much as a full pH unit lower.

Considerations of ease of preparation and cost argue for a practical upper limit of about 50 amino acids in length for the embedder peptide.

3. Amino Acid Composition of Embedder Peptide

The embedder peptide is composed of two types of amino acids. Amino acids of one type have a lipophilic side chain, and amino acids of the other type have a carboxylic acid side chain.

Amino acids having a lipophilic side chain are referred to as lipophilic amino acids, and in peptide sequences they are designated herein with the single letter: L. At least 90%, and preferably 100% of the lipophilic amino acids in a given embedder peptide should be selected from the group consisting of: leucine, isoleucine, norleucine and methionine. From the standpoint of ease of assembly into peptides, commercial availability, and cost, leucine is generally the preferred lipophilic amino acid.

The approximate range in numbers of lipophilic amino acids relative to the number of carboxylic acid side chains in the embedder peptide sequence are tabulated below.

| Number carboxylic acid side chains | Number of lipophilic amino acids (L) |
| --- | --- |
| 6 | 8 to 16 |
| 8 | 11 to 20 |
| 10 | 14 to 24 |
| 12 | 17 to 28 |

Amino acids having a carboxylic acid side chain, other than the one closest to the entry end, should be glutamic acid (single letter designation: E), but not aspartic acid (single letter designation: D). The carboxylic acid moiety closest to that peptide terminus designed to initiate embedding into cell membranes (designated the "entry end") may be the side chain of glutamic acid or may be another carboxylic acid-containing side chain having a structure effective to form a double-hydrogen-bonded acid pair with a nearby glutamic acid side chain in the embedder peptide sequence, such as illustrated in FIGS. 11a and 12b.

4. Acid Pairs of Embedder Peptide

Some years ago it was discovered by applicant that with certain specific separations between two carboxylic acid side chains of a peptide existing in an alpha helical confirmation, in aqueous solution under mildly acidic conditions those two carboxylic acids can cooperatively deionize and form a non-ionic double-H-bonded acid pair structure which serves to mask the polar sites of the two carboxylic acids, as illustrated in FIG. 4a. Carboxylic acid pairs with these specific separations are designated "acid pairs" and are defined supra. When a suitable number of such acid pairs are present and properly positioned along the peptide backbone, then in combination with intervening amino acids having appropriate lipophilic side chains, on acidification the resultant peptide can undergo a surprisingly sharp transition to a non-ionic lipophilic form at a pH up to about 2 pH units higher than the pH where typical carboxylic acids of peptides transition between their anionic and free-acid forms. It is the hydrogen-bond-mediated masking of the polarity of carboxylic acid moieties in these acid pairs which is essential for generating sufficient lipophilicity for entry of embedder peptides into membranes at a pH present or achievable in acidic areas of tumors. Because of constraints imposed by the structure of a peptide in its alpha helical form, such pairs of acids can only form three specific acid pair types. In one acid pair type, designated EE (where E represents glutamic acid), no amino acid intervenes in the peptide backbone between the carboxylic acid side chains forming the acid pair. In another acid pair type, designated EXXE (where X is an amino acid other than glycine or proline), two amino acids intervene in the peptide backbone between the carboxylic acid side chains forming the acid pair. In the third acid pair type, designated EXXXE, three amino acids intervene in the peptide backbone between the carboxylic acid side chains forming the acid pair. FIG. 4b shows a two-dimensional depiction of such a double-hydrogen-bonded carboxylic acid pair structure in a peptide sequence where there are two amino acids intervening between the paired carboxylic acid side chains of two glutamic acids (EXXE acid pair type). For the demanding case of peptide entry into membranes of cells in acidic areas of tumors, the intervening amino acids must be lipophilic. Thus, the acid pairs suitable for embedder peptides of the instant invention are: EE, ELLE, and ELLLE.

It has been found that in order to afford adequate aqueous solubility at the pH in normal tissues, but embedder activity at pH values present in acidic areas of tumors, the embedder peptide should contain at least three acid pairs, with the upper limit on number of acid pairs being dictated by cost and other practical considerations. As noted above, the two carboxylic acids of an acid pair should be separated by zero, two, or three intervening lipophilic amino acids.

5. Axial Distribution of Acid Pairs in Embedder Peptide

Applicant has found that most peptides containing three or more carboxylic acid pairs and an amino acid composition of greater than 50% lipophilic amino acids will rapidly aggregate in acidic aqueous solution. Such rapid aggregation appears to strongly compete with entry into cell membranes, rendering such rapidly-aggregating peptides poorly effective for embedding into cells in acidic areas of tumors. However, this problem of rapid aggregation can be considerably reduced by utilizing amino acid sequences which provide a fairly balanced distribution of acid pairs about the helical axis of the embedder peptide in its alpha helical confirmation.

In a peptide alpha helix each consecutive amino acid side chain is rotated 100 degrees about the helical axis relative to the previous amino acid side chain. Thus, 3.6 amino acids give one full turn of the peptide backbone around its helical axis. To facilitate design of embedder peptides, amino acid side chain positions can be plotted on a spiral graph wherein each successive numbered amino acid side chain position is rotated 100 degrees about the helical axis relative to the previous amino acid side chain, and each successive amino acid side chain is plotted a standard increment further out from the helical axis relative to the previous side chain in the peptide. Using such plots, the two carboxylic acids of each acid pair are then connected by a bold line to allow visualization of the distribution of the acid pairs of an embedder peptide in two dimensions, both with respect to their distribution around the helical axis and with respect to their distribution along the length of the peptide helix.

FIG. 5a shows both the sequence and the axial distribution plot of acid pairs for two peptide sequences wherein the acid pairs are positioned largely on just one side of the peptide's helical axis. Such peptides suffer from rapid aggregation and poor embedder activity. FIG. 5b shows the sequence and the axial distribution plot of acid pairs for two preferred embedder peptide sequences wherein the acid pairs are more evenly distributed about the helical axis. These latter embedder peptides are slower to aggregate under acidic conditions and thus are considerably more effective for embedding into membranes of cells in acidic areas of tumors.

When one considers only embedder peptides which have a high enough pT value to transition to their lipophilic form in acidic areas of tumors, applicant's recent molecular modeling studies and octanol/buffer partitioning experiments with test peptides, carried out in support of the instant invention, suggest that in order to avoid undue aggregation of such high-pT embedder peptides under acidic conditions, for most cases the axial center point of an acid pair should be rotated relative to the axial center point of the next acid pair (designated the "axial rotation between pairs") by a defined number of degrees selected from the group consisting of 450, 500, 550, 600 and 650, and the average of all axial rotations between pairs for a given embedder peptide should be in the range of about 450 to about 600 degrees. These five defined values for axial rotations between pairs correspond to 1.25, 1.39, 1.53, 1.67, and 1.81 helical turns, respectively, between the axial center points of consecutive acid pairs.

While the above rules hold for most cases, different axial rotation values should be used when EE type acid pairs are mixed with ELLE or ELLLE type acid pairs in a given embedder peptide. This is because the EE acid pair doesn't span from one helical turn of the peptide to another, while the ELLE and ELLLE acid pairs do. Thus, for cases where an EE acid pair is adjacent to an ELLE acid pair in the peptide, the axial rotation between those adjacent pairs should be 700 degrees, and where an EE acid pair is adjacent to an ELLLE acid pair the axial rotation between those adjacent pairs should be 750 degrees. FIG. 10 shows both the sequence and the axial distribution plot of acid pairs for representative embedder sequences with such mixed acid pair types.

While the above rules generally apply for embedder peptide sequences suitable for use in acidic areas of tumors, recent experimental results with mammalian cells, carried out in support of the instant invention, suggest that when the average of the axial rotations between pairs in an embedder peptide is no more than 500 degrees, then the pE value is such that embedder activity will likely be limited to only the most-acidic areas of a tumor furthest from capillaries. Likewise, when the embedder peptide sequence contains between about 40% and about 45% acid side chains, the pE value for said embedder peptide is also such that embedder activity will likely be limited to only the most acidic areas of tumors. For such embedder peptides, activity in a greater range of acidic areas of tumors can be achieved in vivo by pre-treating with a substance effective to further reduce the pH in acidic areas of tumors, as described herein in Section V. part B. Thus, to achieve activity in a broad range of acidic areas of a tumor one has the option of developing an embedder peptide with a relatively high pE value, or using an embedder peptide with a lower pE value and decreasing the pH in the acidic areas of the tumor by treating the subject with a substance, such as glucose, which is effective to selectively further reduce the pH in acidic areas of tumors.

A systematic method has been developed for selecting embedder peptide sequences of the instant invention. As a basis for this method, FIG. 6 illustrates the key structural features of acid pair type and values of axial rotations between acid pairs used in selecting prospective amino acid sequences for embedder peptides. Using these key features, Example 1 and FIG. 7 illustrate a simple graphical procedure for selecting suitable embedder sequences. FIG. 8 shows three sets of embedder sequences, where the acid pairs within a single embedder peptide are of a single acid pair type. Acid pairs in the first set are all separated by 500 degree rotations. Acid pairs in the second set are all separated by 550 degree rotations. Acid pairs in the third set are all separated by 600 degree rotations.

As noted previously, a mixture of acid pair types and a mixture of axial rotation values can be used in the same embedder component. FIG. 9 shows both the sequence and the axial distribution plot of acid pairs for representative embedder sequences with mixed rotation values. FIG. 10 shows both the sequence and axial distribution plot of acid pairs for embedder peptides containing mixed acid pair types which include EE pairs.

6. Preferred Amino Acid Sequence Motifs in Embedder Peptide

In experimental work carried out to support the instant invention, it has been found that peptides which include particular sequence motifs often give exceptionally good embedder properties. Those properties include: a particularly high pE value; a sharp transition between the ionic and non-ionic forms; and, a minimal propensity to aggregate under acidic conditions. Two particularly preferred 16-amino acid sequence motifs are: ELLLELELLELELLLE and ELLELELLLELELLEL. The preferred embedder composition below contains an embedder peptide sequence which includes both of these preferred sequence motifs (the motifs are shown positioned above and below the full embedder peptide sequence).

```
        ELLLELELLELELLLE (motif)
Cargo-SELLELELLLELELLELELLLELELLELELLLELL(-NH-CH2-CH(CH3)2)
        ELLELELLLELELLEL (motif)
```

Each of these preferred sequence motifs contains 37.5% E and has an axial rotation between acid pairs of 550 degrees. It is noteworthy that a comprehensive search of the GenBank peptide and protein database (http://www.ncbi.nih.gov/protein) showed that neither of these preferred 16 amino acid sequence motifs are present in any know peptide or protein sequence deposited in that database (based on a search of all 787,608,532 amino acid letters of sequences deposited in this database as of 10 Feb. 2005).

7. Entry End of Embedder Peptide

It has been found that for an embedder peptide to readily enter a cell at a pH as high as that found in acidic areas of tumors, which is generally about pH 6.0 to about 7.0, it is necessary to make that terminus of the embedder peptide which is to first enter the membrane (designated the "entry end") fairly lipophilic. This includes rendering that terminus predominantly non-ionic at the pH in the acidic area of the tumor. In this regard, it has been found that relatively simple structural modifications to the terminus of an embedder peptide can substantially enhance its entry into cell membranes at pH values present in acidic areas of tumors. Adequate lipophilicity of the entry end can be achieved in a number of ways, such as described below.

When the C-terminus is to be the entry end, the normal C-terminal alpha carboxylic acid moiety typical of natural peptides and proteins can be replaced with a carboxylic acid side chain having a structure effective for forming a double-hydrogen-bonded acid pair structure with a nearby glutamic acid side chain, as illustrated in FIG. 11*a*. FIG. 11*a* shows the C-terminal entry end of a 22 amino acid-long embedder peptide, wherein at acidic pH the carboxylic acid of a C-terminal beta-alanine forms an acid pair with a nearby glutamic acid side chain. A C-terminal gamma-amino butyric acid can also be used for this same purpose. Alternatively, the normal C-terminal alpha-carboxylic acid typical of natural peptides and proteins can be rendered non-ionic by converting it to a lipophilic amide, as shown in FIG. 11*b*. Still greater lipophilicity can be obtained by also incorporating up to about three lipophilic amino acids at the C-terminus. FIGS. 11*c* and 11*d* show structures having the same core embedder sequence, but with one and two leucines, respectively, added to the C-terminus, along with the terminal lipophilic amide described above. FIG. 11 also tabulates the relative effects these various C-terminal modifications have on the pH at which these embedder peptides embed into cell membranes (designated the "pE value", which is defined as the pH at which half of the embedder peptides have entered into cell membranes in the membrane binding assay described in Example 6).

When the N-terminus is to be the entry end, the normal N-terminal alpha amine moiety typical of natural peptides and proteins can be capped with a lipophilic group, such as the pivalyl moiety, as illustrated in FIG. 12*a*. Still greater lipophilicity can be obtained by also incorporating up to about three lipophilic amino acids at the N-terminus. FIG. 12 illustrates two preferred lipophilic structures when the entry end is the N-terminus. In FIG. 12*b* a novel acid side chain serves to form an acid pair with a nearby acid side chain of glutamic acid. Such structures are easily prepared using pivalic anhydride or 3,3-dimethyl glutaric anhydride, as described in Example 2.

8. Chirality of Amino Acids in Embedder Peptide

At least 90%, and preferably 100% of the amino acids of a given embedder peptide should have the same chirality so that the embedder peptide will exist largely in its alpha helical confirmation. While embedder peptides having amino acids with L chirality (the chirality of nearly all natural amino acids) can be acceptable, embedder peptides with D amino acids, which are more expensive than L amino acids, provide the advantage of being stable to most proteases and peptidases in the body, thereby helping to assure that the embedder peptide won't become separated from its cargo. Such resistance to enzymatic cleavage can be desirable when the cargo is a toxic substance which, if separated from its embedder peptide, might damage cells in normal tissues.

9. Summary of Preferred Properties of Embedder Peptide

To summarize the characteristics of embedder peptides of the instant invention:

i) the length should be at least about 16 amino acids, and preferably between about 22 and about 33 amino acids;

ii) the embedder peptide should contain at least three, and preferably four to six acid pairs, where acid side chains of a pair are separated by zero, two, or three amino acids in the peptide backbone;

iii) each acid of the acid pairs, except for the acid closest to the entry end, should be a side chain carboxyl moiety of glutamic acid;

iv) the acid side chain closest to the entry end should be a side chain carboxyl moiety of glutamic acid or another carboxyl-containing side chain effective to form an acid pair with a nearby glutamic acid side chain;

v) less than 45% of the amino acids in the core peptide sequence should be glutamic acids;

vi) at least 90%, and preferably 100% of the non-acidic amino acids should be lipophilic amino acids selected from the group consisting of: leucine, isoleucine, norleucine, and methionine;

vii) the axial rotation between the center point of one acid pair relative to the center point of the adjacent acid pair along the alpha-helical peptide backbone should be selected from the group consisting of 450, 500, 550, 600, and 650 degrees, with 550 degrees particularly preferred, except the axial rotation between an EE acid pair and an ELLE acid pair should be 700 degrees and the axial rotation between an EE acid pair and an ELLLE acid pair should be 750 degrees;

viii) the average of all axial rotations between pairs within a given embedder peptide should be at least 450 degrees, but not more than about 600 degrees;

ix) the entry end of the embedder peptide should be modified to make it more lipophilic than in typical peptides and proteins, and it should be predominantly non-ionic at a pH within the acidic areas of a tumor; and, x) at least 90%, and preferably 100% of the amino acids of the embedder peptide should be of the same chirality.

B. Cargo Component of Embedder Composition

The cargo component of the embedder composition has two key functions. One key function is to prevent the cargo from being pulled through the cell membrane by the embedder peptide. It is this function which distinguishes embedder compositions of the instant invention from related transporter compositions. The other key function of the cargo component of an embedder composition is to provide one or more cargo moieties effective for detection or killing of cells in whose membranes the embedder peptide has embedded.

1. Cargo for Diagnostic Application (Diagnostic Moiety)

Desirable properties for a cargo which is to serve for diagnostic applications are:
 a) it should not unduly reduce aqueous solubility, as is needed for effective distribution throughout the body;
 b) it should not be so large that it cannot pass from capillaries into the interstitial space of tumors;
 c) it should not be so large that it cannot be effectively cleared from normal tissues and excreted from the body;
 d) it should not have a significant affinity for cell membranes at the extracellular pH in normal tissues; and,
 e) it should be readily detectable in an appropriate assay or with suitable equipment.

For such applications as research in tumor-bearing small animals, a cargo for diagnostic applications can be as simple as a fluorescent tag, such as a carboxyfluorescein or tetraethylrhodamine. Such fluorescent-tagged embedder compositions localized in acidic areas of tumors can be visualized in live mice by whole-body detection procedures known in the diagnostics art, or visualized more precisely by excising the tumor-bearing tissue and observing thin slices with a fluorescent microscope, as described in Example 8. Embedder compositions localized in tumors can also be extracted from the tissue and quantitated using a spectrofluorometer.

For non-destructive detection of embedder composition in tumors in larger animals, including humans, the cargo component of the embedder composition should generate a signal which is detectable from outside the body. Such signal-generating substances for this purpose are well known in the diagnostics art, and include such substances as radioisotopes (eg., technetium-99 and copper-64) and magnetic resonance contrast agents (eg., gadolinium). Incorporation of such signal-generating cargos into the embedder composition can be via attachment of any of a variety of known multi-dentate chelator moieties to the embedder peptide by a covalent link, followed by addition of the signal-generating radioisotope.

2. Cargo for Therapeutic Application (Therapeutic Moiety)

Desirable properties for a cargo which is to serve for therapeutic applications are:
 a) it should not unduly reduce aqueous solubility, as is needed for effective distribution throughout the body;
 b) it should not be so large that it cannot pass from capillaries into the interstitial space of tumors;
 c) it should not be so large that it cannot be effectively cleared from normal tissues and excreted from the body;
 d) it should not have a significant affinity for cell membranes at the extracellular pH in normal tissues; and,
 e) it should be effective for killing cells into whose membranes the embedder peptide has embedded.

Direct-acting therapeutic cargos include suitable radioisotopes, such as Cu64 and Re188, as well as elements which can be rendered radioactive in situ, such as non-radioactive boron that can be activated by a neutron beam. With proper selection of the radioisotope, the damage from decay products emanating from such cargos can be largely confined to cells in close proximity to the cargo, and so the damage is limited primarily to cells of the tumor.

Indirect-acting therapeutic cargos include moieties which act to recruit the body's normal cell destruction processes. Typical cargos of this type include various peptide sequences, carbohydrates, and other moieties recognized by the body's immune system, particularly the innate immune system. Another indirect-acting cargo, illustrated in FIGS. 15b, 16b, and 18, is the phosphoserine moiety, which serves as a signal to macrophages to engulf and destroy cells displaying this moiety on their outer surface. For such cargos which recruit the body's extracellular cell destruction mechanisms, it is essential that the cargo remain on the outer surface of the cell and not be pulled into the cytosol of the cell. Thus, for such therapeutic cargos the compositions must function in the embedder mode (illustrated in FIG. 1), and not in the transporter mode (illustrated in Comparative FIG. 1a [RELATED ART]).

3. Non-Embedder Segment

While many prospective cargos are so large and/or hydrophilic they cannot be pulled through the cell membrane by the embedder peptide, some useful cargos, such as carboxyfluorescein and tetraethylrhodamine, are small and relatively lipophilic and so have the potential to be pulled by the embedder peptide through a cell membrane into the cytosol. Thus, in such cases where the cargo itself does not provide adequate resistance to being pulled across a cell membrane, in order to assure that the composition functions in an embedder mode (where the cargo remains on the outer surface of the cell) and not a transporter mode (where the cargo enters the cytosol of the cell), the cargo component should include additional polar moieties sufficient to prevent passage of the cargo across the cell membrane. Polar groups for this purpose can be incorporated into the embedder composition simply by adding several polar amino acids to the non-entry end of the embedder peptide, as illustrated in FIG. 13b. Those added amino acids are designated a "non-embedder segment". Typically the amino acids in a non-embedder segment have polar side chains, which may be ionic, and can include, but are not limited to: glycine, alanine, serine, asparagine, glutamine, and aspartic acid, with aspartic acid particularly preferred because it generally remains largely anionic in even the most acidic areas of tumors. A representative non-embedder segment generally effective to prevent cargos from being pulled across membranes can be as simple as several closely spaced aspartic acids. A non-embedder segment may also contain one or more lysines or cysteines, whose side chain amine or sulfhydral, respectively, allows derivatization with a cargo moiety, or with another moiety, such as a sugar, that serves to resist passage of the embedder composition across cell membranes. When desired, a non-embedder segment can also serve to distance the cargo from the surface of the cell in which the embedder peptide is embedded.

C. Linkage of Cargo to Embedder Peptide or to Non-Embedder Segment

Cargos of the invention are preferably linked to the embedder peptide or the non-embedder segment by any of a wide variety of methods and through a wide variety of linkage types, FIGS. 15 and 16 illustrate several preferred linkage types.

For many cargos it is particularly convenient to link the cargo to the N-terminal alpha amino moiety of the embedder peptide via an amide or carbamate link while that peptide is still on its synthesis resin and its side chain carboxyl moieties are still in the protected form, as illustrated in FIGS. 15a and 15b. Alternatively, cargos can be attached via a thioether linkage to either an N-terminal or to a C-terminal sulfhydral. Still another convenient way to a attach a cargo is to add a lysine or cysteine amino acid at the terminus distal from the entry end of the embedder peptide, and then, following cleavage of the peptide from its synthesis resin and cleavage of side chain protective groups, use the side chain amine or sulfhydral, respectively, for linking to the cargo, as illustrated in FIGS. 16a and 16b.

An alternative method for adding a cargo is to add several amino acids to the embedder peptide on the end distal to the entry end, such that the added amino acids are effective to strongly complex with a subsequently added cargo. This strategy is illustrated for the case of a technetium cargo in FIG. 16*c*.

D. Embedder Compositions with Multiple Cargos and/or Multiple Embedder Components It can be desirable to attach multiple cargos to a single embedder peptide, particularly for diagnostic applications. This can be conveniently achieved by incorporating multiple lysines into a non-embedder segment. After deprotection of the lysine side chains, cargos can be attached via amide or carbamate linkages to the amine moieties of each of the lysine side chains, as illustrated in FIG. 16*a*.

Alternatively, for relatively large cargos, such as proteins and small nano-particles, multiple embedder components can be attached to each large cargo.

E. Size of Embedder Compositions

While brain, liver, intestine, and tumors are the exception, typically capillary walls in most tissues, including the kidneys, readily allow substances smaller than about 60,000 daltons to passively cross into the interstitial space (or into the urine in the case of the kidneys), but largely block the passive passage of substances larger than about 70,000 daltons. Since the kidneys are generally the principal route for excretion of the embedder composition in vivo, in order for the kidneys to efficiently excrete an embedder composition from the body that composition should be smaller than about 70,000 daltons, and for the relatively fast excretion desired in diagnostic applications it is recommended that the embedder composition be smaller than about 30,000 daltons.

These size considerations are particularly relevant in considering embedder compositions with multiple cargos or multiple embedder components. Thus, multi-cargo and multi-embedder type embedder compositions larger than about 50,000 daltons should be carefully tested in animals to assure that of the dose administered, that portion which is not embedded into membranes of cells in acidic areas of tumors can be effectively cleared from the body at a practical rate.

F. Precursor Form of the Embedder Composition

For many applications, a user of the embedder composition of the instant invention will obtain a precursor form of that embedder composition. Just before use, that precursor form of the embedder composition will be combined with a radioactive substance to generate the complete embedder composition, which will then be administered to the subject, such as an experimental animal or a patient. This formation of the completed embedder composition just prior to use is generally necessary when the radioactive substance which is to be a part of the cargo component has a short half life and so is only available just prior to its use. Such a precursor form of the embedder composition includes a chelator moiety effective to bind the radioactive substance. When said precursor form is contacted with said radioactive substance, the full embedder composition is formed. For example, in current practice well known in the nuclear medicine art, just before use technetium 99 is collected from a column of molybdenum, and then, after brief chemical processing, the technetium is quickly reacted with a suitable chelator moiety and the resulting product promptly administered to the subject. For the case of the instant invention, said suitable chelator moiety is the precursor form of the embedder composition. FIGS. 15*a*, 16*a*, and 16*c* illustrate as the final step in synthesis of an embedder composition a representative conversion of a precursor form of the embedder composition to a full embedder composition.

G. Representative Embedder Compositions

FIG. 13*a* shows the embedder peptide sequences and their axial distribution plots of acid pairs for a set of 4 simple embedder compositions, each with a representative multi-ionic therapeutic cargo component that prevents transport across cell membranes.

FIG. 13*b* shows a related set of more complex dual-anchor embedder compositions designed for anchoring on both sides of the plasma membrane of a cell in the acidic area of a tumor. These dual-anchor compositions have a sufficiently long embedder peptide to allow penetration of the entry end into the cytosol of the cell and ionization of two carboxylic acid moieties therein. It is these two ionized carboxyls that serve to anchor the entry end of the embedder segment within the cytosol of the cell. These dual-anchor compositions also contain a highly polar non-embedder segment which serves to prevent even a lipophilic cargo from being pulled through the membrane into the cytosol. As noted earlier, such a highly polar non-embedder segment is not necessary in cases where the cargo itself is sufficiently large and/or polar to resist being pulled through the membrane into the cytosol of the cell. These dual-anchor embedder compositions are particularly valuable in applications wherein embedding occurs while the pH in hypoxic areas of tumors is temporarily reduced to enhance embedder activity, as described herein in Section V, part B. It is noteworthy that these longer embedder peptides have the added advantage of undergoing the transition between ionic and non-ionic forms at a somewhat higher pH than is the case for the shorter embedder peptides shown in FIG. 13a.

H. Summary of Key Features of Embedder Compositions

The following is a summary of the key features of an embedder composition. Specifically, an embedder composition comprises:

(a) an embedder peptide which is poly-anionic at pH 7.2 and above, and that converts to a lipophilic form effective to embed into the membranes of cells at a pH below 7.2 that is present in acidic areas of a tumor, said embedder peptide containing (i) a peptide sequence ranging in length from about 16 to about 50 amino acids, (ii) wherein said peptide sequence contains at least three acid pairs, where said acid pairs except for the acid pair closest to the entry end are selected from the group consisting of EE, ELLE, and ELLLE, (iii) each acid of the acid pairs of said peptide sequence except for the acid closest to the entry end is a side chain carboxyl of glutamic acid, (iv) the acid closest to the entry end is selected from the group consisting of a side chain carboxyl of glutamic acid and another carboxyl-containing side chain effective to form an acid pair with a nearby glutamic acid side chain, (v) the number of acid side chains in said peptide sequence is less than 45% of the total side chains in said peptide sequence, (vi) in said peptide sequence the axial center point of one acid pair relative to the axial center point of the adjacent acid pair along the alpha-helical peptide backbone is rotated by a number of degrees selected from the group consisting of 450, 500, 550, 600, and 650 degrees, except for the rotation between an EE acid pair and an ELLE acid pair which is 700 degrees, and the rotation between an EE acid pair and an ELLLE acid pair which is 750 degrees, (vii) the average of the axial rotations between acid pairs in said peptide sequence is at least 450 degrees, (viii) at least 90% of the non-acid side chain amino acids of said peptide sequence are lipophilic amino acids selected from the group consisting of leucine, isoleucine, norleucine and methionine, (ix) the entry end of said peptide sequence is predominantly non-ionic at a pH that is present in acidic areas of a tumor, (x) at least 90% of the amino acids of said peptide sequence are of the same chirality; and, (b) a cargo component which prevents passage across cell membranes, and which contains at least one moiety selected from the group consisting of a diagnostic moiety and a therapeutic moiety.

II. Preparation of Representative Embedder Compositions

Methods for preparing peptides, including the embedder peptides of the instant invention, are well known in the art, and highly refined peptide assembly methods are widely described in the scientific literature, as well as in commercial sources such as the Nova Biochem Handbook and Catalog (Nova Biochem is an affiliate of Merck, KGaA, Darmstadt, Germany). In addition, a number of commercial entities will prepare specified custom-sequence peptides on request at reasonable prices.

In addition to the above generic methods for preparing peptides, Example 2 describes specific methods used for preparing representative embedder peptides of the instant invention, where the embedder peptides have preferred entry ends and have suitable sites for adding a variety of different cargo components. For simplicity, the peptide syntheses described herein used standard FMOC (fluorenyl methoxy carbonyl) peptide synthesis methods, but t-BOC (t-Butoxycarbonyl) syntheses or block assembly methods can also be used.

A. Embedder Composition with a C-Terminal Entry End

Example 2a describes two alternative methods for generating C-terminal entry ends. One method entails preparation of the peptide wherein the alpha-carboxyl of the C-terminal amino acid is linked to the synthesis resin via an ester linkage. After peptide assembly, the peptide is then cleaved from the synthesis resin using a suitable lipophilic primary amine. This generates a lipophilic amide on the entry end, as illustrated in FIGS. 11b, 11c, and 11d. An alternative method entails adding a pre-formed entry end to a Wang-type synthesis resin via an ester link to the gamma carboxyl of a glutamic acid, as illustrated in FIG. 14. The peptide is then cleaved from the resin by the standard TFA (trifluoroacetic acid) procedure. In both of these methods the N-terminal end is reserved for attachment of the cargo component containing one or more cargos. FIG. 15a illustrates on-resin N-terminal attachment of a representative cargo component for diagnostic application, and FIG. 15b illustrates how to attach a representative cargo component for therapeutic application.

B. Embedder Composition with an N-Terminal Entry End

Example 2b describes methods for generating two preferred N-terminal entry ends, as shown in FIG. 12, as well as incorporation of moieties near the C-terminus suitable for subsequent attachment of one or more cargo components. Methods by which one can attach cargos near the C-terminus are illustrated in FIGS. 16a and 16b.

III. Assessment of Properties of Embedder Composition

It is recommended that in order to develop an optimal embedder composition containing a selected cargo it is prudent to first prepare a variety of prospective embedder peptides, and then employ a series of increasingly complex assays to progressively narrow these down to one or a few which are best for a particular application. First testing a variety of prospective embedder peptides in simple, fast, and quantitative assays allows one to efficiently select the most promising amino acid sequences and entry ends for the embedder peptide. Then, after adding prospective cargo components, substantially fewer additional tests should be required to achieve effectiveness in vivo.

A. Partitioning and Aggregation Studies of Embedder Peptide

It is recommended that initial studies on prospective embedder peptides, typically labeled on their non-entry end with a suitable fluor such as carboxyfluorescein, should generally entail partitioning between n-octanol (which emulates the lipophilic interior of cell membranes) and a range of suitable buffers (emulating the extracellular medium within tumors and normal tissues), as described in Example 5a. This allows one to easily and quantitatively compare various embedder peptides with respect to the pH at which each converts from its anionic polar form to its non-ionic lipophilic form (the mid-point of this transition is referred to as the pH of transition, or pT value). It also allows one to easily compare the various embedder peptides with regard to how sharp the transition is between their anionic and lipophilic forms.

It is also desirable to compare the tendency of the different embedder peptides to aggregate as a function of pH. A suitable assay to assess aggregation as a function of pH is described in Example 5b.

B. Binding Studies with Red Cell Ghosts

In the course of applicant's earlier development of peptides designed to transport substances from a low-pH environment across a lipid layer to a higher-pH aqueous compartment, described in U.S. Pat. No. 6,030,941, it was assumed that the pH at which the peptide converted from its anionic form to its lipophilic form in octanol/buffer partitioning assays provided a good estimate of the pH at which that peptide would enter a cell membrane. However, in the course of subsequent, more extensive studies in support of the instant invention, applicant has discovered that the pH value at which related embedder peptides of the instant invention convert between their anionic form and their lipophilic form in octanol/buffer partitioning studies (the pT value) is significantly higher, on the order of about 0.5 to 1.0 pH unit, than the pH at which the embedder peptides will embed into a mammalian cell membrane (designated the "pE value"). The discrepancy between the pT value from a partitioning study and the pE value from a membrane embedding study is probably because in a partitioning study when the peptide has lost some of its ionic charges its entry into the octanol phase can begin, and once begun, the further conversion of the partially-ionic peptide to its non-ionic lipophilic form is favored by the lipophilicity of the octanol phase it is entering.

In contrast, in order to begin entry into a cell membrane, it is probable that at least the entry end of the peptide must lose all of its multiple anionic charges before it can closely approach the anionic cell surface into which it is to embed. Thus, pT values obtained from partitioning studies are primarily useful only for determining the relative order of the embedder peptides with respect to the pH at which they will transition between hydrophilic and lipophilic forms, as well as the sharpness of that transition. However, binding assays utilizing actual mammalian cell membranes to obtain pE values, such as is described in Example 6, are generally essential for selecting an optimal embedder peptide for a given application.

It should be noted that besides pH, it has recently been discovered that temperature also has a substantial impact on the ability of an embedder peptide to embed into cell membranes. Therefore, membrane binding studies and cell embedding studies should not be carried out at room temperature, but instead should be carried out at the temperature at which the developed product will be used. This is 37 degrees C. when the embedder composition is to be used in humans.

Example 6 details a simple method to determine the pH at which a given embedder peptide will embed into a representative cell membrane (the pE value). This red cell ghost assay is fast, easy, and gives precise quantitative results which appear to correlate well with results from similar studies in cultured cells. Preliminary results from in vivo studies also suggest that the pE values determined with red blood cell ghosts are predictive of embedder activity in tumors in live animals.

C. Embedder Studies with Cultured Cells

It is desirable to test both prospective embedder peptides and prospective full embedder compositions with cultured cells before moving to the more complex in vivo testing phase. It is recommended that the prospective embedder peptides containing just a fluorescent moiety for the cargo be tested first for embedding into the membranes of cultured cells, in order to narrow the selection to just a few of the more promising structures. Only then should full embedder compositions be prepared and tested in cultured cells.

Because even within a given tumor there is considerable heterogeneity in the permeability of the capillaries, the interstitial space in some regions of a tumor can contain considerable serum protein, while the interstitial space in other regions of the tumor may be relatively free of serum proteins. Since different embedder peptides appear to have differing affinities for serum proteins, particularly when the embedder peptides are in their non-ionic lipophilic form, it is prudent to compare embedding into the membranes of cultured cells by prospective embedder peptides both in culture medium free of serum, and in culture medium containing about 5% to 10% of serum.

As described in Example 7, it is recommended that the initial embedder studies with cultured cells entail preparing fluorescein-tagged embedder peptides, each in a series of culture media buffered at varying pH values ranging from about pH 6.0 (to emulate the most acidic regions of tumors) through 7.2 (to emulate the lowest pH typically found in normal tissues). The cultured cells, typically Hela, are then exposed to each embedder-containing medium for about 1 to 2 hours at 37 degrees C., washed with medium of the same pH but free of embedder composition, and then the cells viewed under a fluorescent microscope to assess the amount and disposition of the fluorescent tag associated with the cells.

After treatment with embedder peptide, the living cells, without fixation, should preferably be viewed with an inverted microscope. This allows one to distinguish between fluorescence which is only on the cell surface and which gives a halo appearance, and fluorescence which is within the cytosol/nuclear compartment and which is most dense where the cell is thickest. If the fluorescence from the embedder peptide appears to be within the cytosol of the cells, this suggests that the cargo component is not sufficiently large andlor polar to prevent entry of the cargo into the cell. Such cytosolic entry can be easily prevented by adding a non-embedder segment comprising several aspartic acids. Alternatively, If the embedder peptide failed to bind to the cells, it is likely that the pE value of the peptide is too low or the cells were not exposed to medium of sufficiently low pH to effect conversion of that particular embedder peptide to its lipophilic form. Once microscopic inspection indicates the desired embedding activity is achieved, a quantitative measure of embedding can be made by dissolving the cells in aqueous 1% sodium dodecylsulfate buffered to pH 9, and the fluorescein moiety quantitated in a spectrofluorometer.

After a number of embedder peptides effective to embed in membranes of cells at the desired pH, preferably about 6.5 to 6.9, have been identified in the above assay, where feasible, the next step is to prepare the full embedder composition and test it in cultured cells.

D. Studies in Tumor-Bearing Animals

The principal applications of the embedder compositions of the instant invention are for detection and treatment of tumors in animals, particularly in humans. Accordingly, it is desirable that the prospective embedder compositions be thoroughly tested in vivo in animals whose physiology closely resembles that of humans in regard to body temperature; interstitial pH in normal tissues; the presence of acidic areas in tumors larger than microscopic size; and, blood clearance mechanisms. Mice satisfy these criteria and further constitute a well-studied model organism often used for tumor studies. It is recommended that the one or a few prospective embedder peptides which excelled in the in vitro and cell culture studies described above next be tested in mice, as described in Example 8.

For initial in vivo testing it is recommended that one first test prospective embedder peptides by injecting each fluorescent-tagged embedder peptide into at least two sets of tumor-bearing mice. After a suitable period of time, typically about 1 to 24 hours to allow washout from normal tissues, one set of mice are then used to assess the distribution of the embedder peptide throughout the organism. This entails removing the test tumor and major organs of the mouse, including liver, kidneys, lung, heart, and the like. After extracting the fluorescent-tagged embedder peptide from those tissues, the extracted fluor is quantitated on a spectrofluorometer. Generally a desirable embedder peptide is one which gives maximal labeling of the tumor, with little or no labeling of other tissues. The other set of mice are then used to assess the detailed spatial distribution of the embedder peptide within the tumors. This procedure entails removing each test tumor, freezing it, taking thin slices of the tumor in a cryostat, and finally viewing the tissue slices under a fluorescent microscope.

The design of subsequent in vivo tests of a full embedder composition will necessarily be dependent on the selected cargo. For instance, if the cargo is a chelated technetium-99 radioisotope, as discussed hereafter in Section VI.A., the final distribution of embedder composition in the animal can be determined in situ by standard scintography.

Alternatively, if the cargo is a phosphoserine moiety designed to signal phagocytic cells to engulf and destroy cells in which the embedder composition is embedded, then it may be desirable to initially generate tumors in the mice by inoculating the mice with transgenic tumor cells expressing luciferase. After tumors have formed, the mice are treated both with the embedder composition to effect destruction of the quiescent tumor cells, and with standard radiation or chemotherapy to effect destruction of the fast-dividing cancer cells. Regression of the tumors is then followed by periodic injection of an ester of luciferin into the mice and monitoring the living mouse for emitted light, which will be emitted by any residual live cancer cells.

IV. Formulation and Administration of Embedder Composition

For use in vivo it is generally desirable that the embedder composition be dissolved in an aqueous isotonic solution. Since the embedder peptides are largely insoluble in aqueous solution when the carboxyl side chains are in their free acid form, a base should be used to neutralize the acid moieties. It has been found that the sodium salt of embedder compositions generally have good aqueous solubility, while salts with organic amines, such as triethylamine, can have poor aqueous solubility. For some of the more lipophilic embedder types, if sodium chloride (NaCl) is used to make the embedder solution isotonic the embedder composition may have inadequate aqueous solubility. Therefore, instead of using NaCl, it is recommended that a suitable non-reducing carbohydrate, such as mannitol, be used to make the solution isotonic. Typically this is done by adding mannitol to a final concentration of about 0.3 Molar.

A representative method for formulating an embedder composition is as follows: Weigh out 20 microMoles of embedder composition in its free acid form (typically about 70 to 100 milligrams). Add 546 milligrams of mannitol, 9.5 milliliters of water, and 0.1 milliliter of 1 Molar aqueous sodium hydroxide (NaOH). Using a pH meter, while rapidly stirring slowly add more 1 M aqueous NaOH to effect complete dissolution of the embedder composition and raise the pH to about 8.0. This typically requires about an additional 0.1 ml of NaOH solution. Generally the embedder peptide of the embedder composition is stable to sterilizing temperatures (about 120 degrees C. for 30 minutes) and so if the cargo component is also stable to these temperatures, the embedder composition solution can be heat sterilized before use. If the cargo component is not sufficiently stable for heat sterilization, the solution can be filter sterilized by passing the solution through a sterile 0.2 micron filter before use.

For long term storage and for shipping it is often desirable to prepare an isotonic near-neutral solution of embedder composition, as above. This is frozen, then freeze-dried, capped, and heat sterilized at, for example, 120 degrees C. for 30 minutes. To use the preparation, simply add an appropriate volume of sterile water and shake to dissolve.

To assure efficient delivery into the vascular compartment of an animal, and particularly a human, and thence distribution throughout the body and into any tumors which are present, it is recommended that the embedder composition be administered by intravenous injection. While the 2 milliMolar embedder solution described above is suitable for most testing purposes, it should be appreciated that suitable concentrations of embedder composition for diagnostic and therapeutic applications are largely dependent on the identity of the cargo, and so should be empirically determined for each embedder composition.

V. Enhancement of Activity of Embedder Composition in Vivo

A. Use of Two or More Embedder Compositions Having Different pE Values

For tumors with acidic areas having a fairly broad range of pH values there is the potential that embedder compositions with too high of a pE value may aggregate or be largely bound to proteins or cell surfaces before reaching the lowest pH areas of the tumor most distant from capillaries. Alternatively, embedder compositions with too low of a pE value may fail to embed into the membranes of cells in areas of higher pH closer to capillaries in the tumor. One strategy for dealing with a wide pH range within a tumor is to use a combination of at least two embedder compositions, one whose embedder peptide has a higher pE value and so is maximally effective in regions of the tumor which have a higher pH, and another whose embedder peptide has a lower pE value and so is maximally effective in regions of the tumor which have a lower pH. The rationale for using such a combination of embedders is that the composition with the higher pE will be effective for embedding into membranes of cells of tumors in areas of higher pH close to capillaries, but may never reach areas of lower pH further from capillaries. Conversely, the composition with the lower pE may be relatively ineffective in areas of higher pH close to capillaries, but will not aggregate or become bound to proteins or membranes in such regions and so can diffuse into and be fully effective when they reach areas of lower pH farther from capillaries.

B. Use of Substance to Selectively Further Reduce pH in Acidic Areas of Tumor

It has long been known that introduction of a rapidly-metabolized sugar, such as glucose, into tumor-bearing mammals acts to reduce the pH in the interstitial space in hypoxic areas of the tumors for about 1 to 2 hours, while having little or no effect on the pH of the interstitial space in normal tissues (Naeslund & Swenson (1953) Acta Obstet. Gynecol. Scand. 32, 359-367; Kozin, Shkarin, & Gerweck (2001) Cancer Research 61, 4740-4743; Prescott, Charles, Poulson, Page, Thrall, Vujaskovic, & Dewhirst (2000) Clinical Cancer Research 6, 2501-2505).

The pH in acidic areas of tumors can also be further reduced by treating with such agents as the mitochondrial inhibitor, meta-iodobenzylguanidine, again without undue effect on the pH in normal tissues (Kuin, Smets, Volk, Paans, Adams, Atema, Jahde, Maas, Rajewsky, & Visser (1994) Cancer Research 54, 3785-3792; Jahde, Volk, Atema, Smets, Glusenkamp, Rajewsky (1992) Cancer Research 52, 6209-6215).

Such substances, used alone or in combination, can improve both the diagnostic and the therapeutic utility of embedder compositions by increasing the proportion of cells of a tumor into which an embedder composition will enter. Alternatively, such induced temporary reductions in the pH within tumors can allow use of embedders with lower pE values, thereby even further improving the ability of the embedder composition to discriminate between tumor and normal tissues.

C. Use of Substance to Minimize Re-Uptake of Embedder Composition in the Kidneys 1. Substance to Block Endocytotic Reabsorption by Proximal Tubules Peptides and proteins smaller than about 60,000 daltons are generally filtered from the blood into the urine in the glomerulus of the kidney. Peptides so filtered are subsequently reabsorbed from the urine by cells of the proximal tubule via receptor-mediated endocytosis. After endocytosis into proximal tubule cells, the peptides are subjected to peptidases and proteases of lysosomes which can lead to sequestering of degradation products within cells of the kidney and/or re-entry of degradation products back into the blood. Retention of degradation products of embedder composition in the kidney may cause nephrotoxicity, and re-entry into the blood may compromise the goal of reducing background signal in normal tissues via excretion of non-tumor-bound embedder composition from the body. If such endocytotic reabsorption by proximal tubules proves to be a significant problem for a given embedder composition, it may be desirable to additionally treat the patient with a substance which is effective to reduce reabsorption of peptides by the proximal tubules, such as D-lysine, thereby speeding clearance of the embedder composition from the body. Use of D-lysine for reducing reabsorption of peptides in the kidney is described in: Bernard, Krenning, Breeman, Rolleman, Bakker, Visser, Macke, de Jong, Journal of Nuclear Medicine 38, 1929 (1997).

2. Substance to Make Urine Alkaline

Urine is often acidic. Embedder composition which has been filtered from the blood into the urine will convert in such acidic urine to its non-ionic lipophilic form, which can then embed into the plasma membrane of cells lining the glomerulus and proximal tubule of the kidney. When the cargo is a diagnostic moiety this re-uptake onto the surfaces of cells of the kidney can limit the ability to detect tumors anywhere near the kidney. When the cargo is a therapeutic moiety this re-uptake onto the surfaces of cells of the kidney has the potential to cause nephrotoxicity. To avoid problems caused by acidity of the urine, the urine can be temporarily rendered moderately alkaline by a number of methods known in the medical arts for acute treatment of acidosis. One widely used method which increases the pH in the urine is simply to feed the patient an appropriate dose of sodium bicarbonate by mouth. This would be done prior to, and possibly during treatment with the embedder composition. This simple measure can assure that the urine remains slightly basic during the time the excess embedder composition not embedded onto cells of tumors is being cleared from the body through the kidneys.

VI. Diagnostic and Therapeutic Applications of Embedder Composition

A. Diagnostic Application

Largely because of the great variability between tumors, routine detection of a wide range of tumor types at a sufficiently early stage that they can be successfully treated, preferably before they show symptoms, has long been an unmet goal of medicine. Much of the difficulty in routine early detection of tumors has been in finding and exploiting some property which is common to most or all tumors, and which can be effectively exploited for routine and affordable detection of very-early-stage tumors. While it has been known for over seventy years that tumors larger than microscopic size contain hypoxic areas wherein the interstitial pH is lower than in normal tissues, until applicant's development of peptides which can sharply transition between poly-anionic and lipophilic forms at a pH present in acidic areas of tumors, this common property of tumors had not been exploited for detecting tumors.

The embedder compositions having diagnostic cargos disclosed herein exploit this interstitial acidity in tumors to provide a new and novel means for detecting tumors. Coupled with modern imaging technologies, these embedder compositions offer the promise of routine detection of a wide range of tumor types. It is envisioned that suitable embedder compositions can be used routinely in annual physical exams for early detection of even very small tumors, allowing their treatment at much earlier stages of tumor development where cure rates are highest.

FIG. 17 shows two representative embedder compositions designed for detection of tumors containing acidic regions. The shorter of the two embedder peptides in these diagnostic compositions undergoes a transition to its lipophilic form at a pH about 0.2 pH unit lower than the corresponding transition of the longer peptide, and so when used together these two compositions may provide better tumor detection than either used alone. In these compositions the embedder peptide is linked to a precursor to the cargo component which contains a chelator moiety effective to strongly bind Technetium. Chelators of this general structure are widely used for binding technetium. After formulation as described in Section IV herein, just before injection into a patient, freshly-prepared radioactive technetium is reduced in situ and the reduced form complexed with the chelator moiety of the precursor form of the embedder composition, as illustrated in FIG. 15a, thereby giving the full embedder composition ready for injection into the patient. Complexing with technetium is preferably carried out in a single step in a single vial using a commercially available kit, such as the Isolink Kit (available from Mallinckrodt, Philipsburg, N.J.).

The technetium-containing embedder composition is next injected into the patient After a suitable period of time to allow for clearance of embedder composition from normal tissues, such as about 1 hour to 24 hours, the patient is scanned with a gamma scintillation camera (standard in modern Nuclear Medicine Departments) to show the position and size of any tumors which are present in that patient.

To increase diagnostic sensitivity and specificity, about 30 minutes before injecting the embedder composition the patient can be pre-treated with a substance, such as glucose or glucose plus meta-iodobenzylguanidine, to further temporarily reduce the pH within acidic areas of any tumors present in the patient.

To minimize endocytotic re-uptake of embedder composition from the urine in the proximal tubules of the kidney, the patient may be pretreated with a substance which is effective to reduce reabsorption of peptides by the proximal tubules, such as D-lysine.

To avoid acid-mediated re-uptake of embedder composition from the urine due to low-pH urine, the patient may be fed an appropriate dose of sodium bicarbonate by mouth prior to, and possibly during treatment with the embedder composition.

B. Therapeutic Application

While rapidly dividing tumor cells can be efficiently killed by conventional radiation and chemotherapy, the slow-dividing and non-dividing tumor cells in acidic areas of tumors are far more resistant to killing by such conventional therapies. While several therapies have been developed to exploit the hypoxia in tumors, to date there appear to be no reports of cancer therapeutics explicitly designed to exploit the acidity within tumors to effect selective killing of quiescent tumor cells while avoiding damage to cells in normal tissues.

The embedder compositions having therapeutic cargos disclosed herein are designed to exploit this interstitial acidity in tumors to provide a new and novel means for selectively killing the normally-treatment-resistant cells in acidic regions of tumors. Coupled with conventional cancer therapies effective for killing fast-dividing tumor cells, said embedder compositions offer the promise of more effective treatment and far fewer relapses for a wide range of tumor types.

FIG. 18 shows two representative embedder compositions designed to induce killing of cells in acidic areas of tumors. As in the diagnostic set in FIG. 17, the shorter of the two embedder peptides in these compositions undergoes a transition to its lipophilic form at a pH about 0.2 pH unit lower that the corresponding transition of the longer embedder peptide, and so when used together these two compositions may provide better therapeutic effect than either used alone. The cargo of these embedder compositions, a phosphoserine moiety, is designed to serve as a cell-surface signal effective to cause phagocytic cells to engulf and destroy the cells in which the embedder composition is embedded. After formulation as described in Section IV, the embedder composition is injected into the patient. Preferably, said treatment with embedder composition is carried out in combination with a conventional cancer therapy to best assure destruction of both quiescent and fast-dividing cells of the tumor.

To increase the therapeutic efficacy, about 30 minutes before injecting the embedder composition the patient can be pre-treated with a substance, such as glucose or glucose plus meta-iodobenzylguanidine, which is effective to further temporarily reduce the pH within acidic areas of any tumors present in that patient.

To minimize endocytotic re-uptake of embedder composition from the urine in the proximal tubules of the kidney, the patient may be pretreated with a substance which is effective to reduce reabsorption of peptides by the proximal tubules, such as D-lysine.

To avoid acid-mediated re-uptake of embedder composition from the urine due to low-pH urine, the patient may be fed an appropriate dose of sodium bicarbonate by mouth prior to, and possibly during treatment with the embedder composition.

EXAMPLES

Example 1

Graphical Method for Identifying Amino Acid Sequences for Embedder Peptide

There are 10 to the 28th power (about a hundred trillion times a hundred trillion) possible amino acid sequences for a peptide just 22 amino acids long and composed of just the 20 standard amino acids used in nature. However, of this vast number of possible peptide sequences, only an infinitesimally tiny fraction (on the order of a few thousand) can effectively serve as an embedder peptide effective in the pH range present in acidic areas of tumors. The following rules and procedures allow one to readily select such embedder peptide sequences from the vast sea of possible peptide sequences which would be ineffective as embedders in acidic areas of tumors. The rules are summarized below.

a) All carboxylic acid side chains of the embedder sequence should be glutamic acids, excepting the carboxylic acid closest to the entry end, which may be either a glutamic acid side chain or some other carboxyl-containing structure effective to form an acid pair with a nearby glutamic acid side chain, such as illustrated in FIGS. 11a and 12b.

b) Every carboxylic acid should have a carboxylic acid pairing partner capable of forming a doubly-hydrogen-bonded acid pair structure selected from the three types shown in FIG. 6a, excepting the acid closest to the entry end may have a different structure, but one which is still effective to form an acid pair with a nearby glutamic acid side chain, such as illustrated in FIGS. 11a and 12b.

c) The acid side chain content in the embedder sequence should be less than 45% of the total side chains.

d) The axial rotation between center points of consecutive acid pairs should be selected from the group consisting of 450, 500, 550, 600, and 650 degrees, as illustrated in FIG. 6b, excepting the rotation between an EE acid pair and an ELLE acid pair should be 700 degrees, and the rotation between an EE acid pair and an ELLLE acid pair should be 750 degrees, as illustrated in FIG. 10.

e) The average of axial rotations between acid pairs in a given embedder peptide should be at least 450 degrees, and preferably at least 500 degrees.

f) At least 90%, and preferably 100% of the amino acids which do not have carboxylic acid side chains should be lipophilic amino acids selected from the group consisting of: leucine, isoleucine, norleucine and methionine.

FIG. 7 illustrates a simple stepwise procedure to apply these rules for selection of embedder peptide sequences. This procedure entails the following steps:

First, mark out positions for at least 16 amino acids, but preferably positions for about 22 to about 30 amino acids.

Second, starting from one end, pencil in one of the three acid pair types and mark its center point.

Third, pencil in a second center point for the next acid pair, with the axial rotation value between these consecutive center points selected from the group consisting of 450, 500, 550, 600, and 650 degrees, as illustrated in FIGS. 8 and 9, or the axial rotation value selected from 700 and 750 degrees for the special cases illustrated in FIG. 10. It should be noted that moving from one amino acid position to the next corresponds to an axial rotation of 100 degrees.

Fourth, using that second center point, enter an appropriate second acid pair, again selected from the three types shown in FIG. 6a.

Continue to add acid pairs in this manner until the peptide sequence contains at least three, but preferably 4 to 6 acid pairs.

Next, fill the intervening amino acid positions with lipophilic amino acids, preferably leucines, as illustrated in FIGS. 7a(iii) and 7b(iii).

The prospective embedder peptide sequence generated above should then be assessed to assure that less than 45% of the side chains of the embedder peptide sequence are acid side chains, and that the average of the axial rotations between acid pairs is at least 450 degrees.

After an embedder peptide sequence has been selected by the above steps, the next step is to pick which end of the peptide (C-terminal or N-terminal) is to be the entry end. Generally either end works equally well, but picking one over the other may significantly affect the required synthetic effort when subsequently adding particular cargo components. FIGS. 11 and 12 illustrate representative entry ends of both the C-terminal and the N-terminal types, and FIG. 14 shows one method for preparing a representative C-terminal entry end. These and closely related entry ends are relatively easy to prepare and suitable for most applications. More complicated end structures can also be used if it is desirable to make the entry end even more lipophilic. However, it should be appreciated that excessive lipophilicity of an entry end can lead to aggregation problems, which ultimately can reduce instead of increase embedder efficiency.

Example 2

Preparation of Representative Embedder Peptides

Embedder peptides used in experimental studies carried out in support of the instant invention have generally been synthesized on a Wang resin using an automated peptide synthesizer provided with fluorenylmethoxycarbonyl-protected/pentafluorophenyl ester-activated amino acids. The C-terminal amino acid of the peptide is typically linked to the synthesis resin via the acid-cleavable ester linkage characteristic of the Wang type resin. Except where noted otherwise, deprotection and cleavage from the resin is with trifluoroacetic acid (TFA), plus triisopropylsilane/water to scavenge carbonium ions generated in the deprotection step. These methods are well known in the art and are detailed in the NovaBiochem Handbook and Catalog, 2000.

a) Embedder Peptides with C-terminal Entry Ends

C-terminal entry ends having one, two, or three C-terminal leucines, and capped with a terminal lipophilic amine, such as shown in FIGS. 11c and 11d, generally give effective entry into membranes.

One convenient way to generate such entry ends is to simply prepare the peptide sequence with the appropriate number of leucines at the C-terminus, and then cleave the peptide from the resin using neat isobutylamine. In this method, the completed peptide, still on the synthesis resin and with side chains still protected, is washed with dichloromethane and dried under vacuum. One gram of the dry resin/peptide preparation is then added to 20 ml of isobutylamine, the container capped tightly, and the preparation incubated at 50 degrees C. for 4 to 6 hours. About once each hour during the course of this incubation the container is inverted several times. The preparation is next filtered into a rotovap flask and the resin washed repeatedly with trifluoroethanol to wash the released peptide, now with a C-terminal isobutylamide, from the synthesis resin. The isobutylamine and trifluoroethanol are rotovaped off in a warm water bath. 100 ml of acetonitrile is added to the peptide residue and rotovaped off. The peptide residue is then treated with trifluoroacetic acid/triisopropylsilane/water in the conventional manner to deprotect the amino acid side chains. For typical peptides ether is used to wash the peptides after deprotection with TFA. However, it is recommended that such standard procedures not be followed, and instead the embedder peptides be washed with a 1:1 mixture of t-butylmethylether:hexane. This is because typically the embedder peptides of the instant invention are fairly soluble in ether and so considerable losses are incurred in the standard ether washing procedure.

For cargo components or precursor cargo components which are stable to the above processing conditions, said components can be linked to the N-terminal amine of the peptide while the peptide is still on the synthesis resin and its side chains still protected, as illustrated in FIGS. 15a and 15b. When the cargo component or precursor cargo component is added to the peptide while the peptide is still on its synthesis resin and side chains still protected, the resultant embedder compositions are typically suitable for experimental use without special purification. However, if the cargo components are not stable to the above conditions, the cargo component should be linked to the N-terminal amine, or to an N-terminal lysine side chain, or to an N-terminal cysteine side chain after the peptide has been fully deprotected. In such cases purification of the product is generally required.

Because of the high concentration of a fairly strong primary amine base at a fairly high temperature for a number of hours, the foregoing procedure for generating a lipophilic amide on the C-terminus may cause some racemization of the peptide (but not observed in our preliminary assays). To preclude such possible racemization, a lipophilic C-terminal amide can be introduced by the method illustrated in FIG. 14. While this alternate route entails greater synthetic effort up front, it has the merit of simpler processing of the final peptide product—generally requiring only the standard deprotection and cleavage from the resin with trifluoroacetic acid/triisopropylsilane/water. This later procedure also offers the advantage of allowing on-resin linking of the cargo component to the N-terminus of the peptide when that cargo component would be damaged by treatment with isobutylamine, but not with TFA, such as illustrated in FIGS. 15a and 15b.

After synthesis and processing, the mass of each embedder composition or precursor to the embedder composition is typically confirmed by disolving about 0.1 mg in 50 microliters of methanol, and then running a matrix assisted laser desorption ionization time of flight mass spectrum.

b) Embedder Peptides with N-terminal Entry Ends

N-terminal entry ends having one, two, or three N-terminal leucines and a pivalamide cap are prepared simply by synthesizing the appropriate peptide sequence, and then, after removing the terminal FMOC protective group, reacting the resin-bound/side chain-protected peptide with pivalic anhydride. After subsequent processing, this gives an entry end structure such as shown in FIG. 12a. Alternatively, N-Terminal entry ends having two or three leucines capped with 3,3-dimethyl glutaryl group, with its built in acid side chain, are prepared simply by synthesizing the appropriate peptide sequence, and then, after removing the terminal FMOC protecting group, reacting the resin-bound/side-chain-protected peptide with 3,3-dimethylglutaric anhydride. After subsequent processing this gives a structure such as illustrated in FIG. 12b.

For embedder peptides which contain an N-terminal entry end, it is typically necessary to provide a suitable handle at or near the C-terminus for attachment of the cargo component or precursor to the cargo component—though this requirement can be circumvented in such cases where the cargo component or a precursor to the cargo component is incorporated into the peptide sequence during peptide synthesis, as illustrated in FIG. 16c.

FIGS. 16a and 16b illustrate a preferred scheme for linking a cargo component to the side chain amine of a C-terminal lysine. A similar scheme can be used to link to the side chain sulfhydral of a C-terminal cysteine. For example, when the cargo component contains a chloroacetamide moiety, or acrylamide moiety such coupling will generate a thioether linkage. These and many other methods for linking cargo components to the embedder peptide are well known in the chemical art, such as described in the book: Bioconjugate Techniques (Hermanson, 1996).

Example 3

Attachment of Representative Cargo for Diagnostics Application

The MAG3 moiety (mercaptoacetic-glycine-glycine-glycine) is a very robust moiety which is widely used for covalently linking to biological structures and subsequently complexing with an added technetium 99. Because of its simplicity, ease of preparation, and ease of attachment to an embedder peptide of the instant invention, use of this moiety is preferred for generating a precursor form of the embedder composition, as illustrated in FIG. 15a. Just before use, that precursor form of the embedder composition is contacted with a suitable preparation of technetium 99 to generate the full embedder composition, and that composition is then injected into the subject for the purpose of detecting tumors in said subject.

Example 4

Attachment of Representative Cargo for Therapeutic Application

A particular merit of embedder compositions for therapeutic application is that they can be designed to exploit the body's natural cell killing mechanisms. Of particular note in this regard is the fact that the phosphoserine moiety of phosphotidylserine is positioned on the intracellular face of the plasma membrane of normal healthy cells. However, if that cell is damaged or stressed or otherwise becomes unsuitable for carrying out its normal functions, the cell undergoes apoptosis (cell suicide), and a key step in that process is the switching of the phosphoserine moieties from the intracellular face of the plasma membrane to the extracellular face of the plasma membrane. The phosphoserine moiety on the extracellular face then acts as a signal to phagocytic cells to engulf and destroy that cell.

In tumors, this apoptosis pathway is generally short-circuited such that even severely abnormal tumor cells generally do not exhibit the phosphoserine moieties on the extracellular face of the plasma membrane. This serves to protect the tumor cells from the body's normal policing of abnormal cells.

By using a phosphoserine moiety as the cargo component of an embedder composition, it is envisioned that the quiescent cells in acidic areas of tumors can again be brought under the control of the body's normal policing of abnormal cells.

Methods for attaching a phosphoserine moiety to an embedder peptide for the purpose of recruiting the body's natural cell killing mechanisms are illustrated in FIGS. 15b and 16b.

Example 5

Biophysical Studies of Embedder Peptide a) Partitioning Between n-Octanol and Aqueous Buffers Partitioning between octanol and aqueous buffer provides information on the pH at which an embedder peptide undergoes the transition between its poly-anionic form and its lipophilic form (the pH of transition, or pT value). For such studies one should prepare the embedder peptide with a fluorescein tag on the end which is distal to the entry end. A 1.0 milliMolar stock solution of this fluorescent-tagged embedder peptide is prepared comprising 1.0 microMole of such embedder peptide, in its free acid form, dissolved in 1 ml of dimethylformamide or isopropanol. These studies are carried out at room temperature.

Prepare the following buffer solutions:

0.1 M 2-(Morpholino)ethanesulfonic acid (MES) (pKa 6.1).

Using 5 M aqueous NaOH, adjust portions to:
 a) pH 5.8
 b) pH 6.0
 c) pH 6.2
 d) pH 6.4

0.1 M N-(2Acetoamido)-2-aminoethanesulfonic acid (ACES) (pKa 6.8).

Using 5 M aqueous NaOH, adjust portions to:
 e) pH 6.6
 f) pH 6.8
 g) pH 7.0

0.1 M 4-(2-Hydroxyethyl)piperazine-1-ethanesulfonic acid (HEPES) (pKa 7.5).

Using 5 M aqueous NaOH, adjust portions to:
 h) pH 7.2
 i) pH 7.4
 j) pH 7.6
 k) pH 7.8

To each of eleven 0.75 ml shell vials add: 5 microLiters of embedder peptide solution
300 microLiters of n-octanol
300 microLiters of one of the above buffer solutions Cap, shake vigorously for 1 minute, then centrifuge to separate the phases.

To each of 22 shell vials add 0.85 ml of base solution (2% tetramethyl guanidine/98% isopropanol, v/v), and then add 150 microLiters of the upper octanol phase from each of the 11 test samples to 11 vials of base solution, mix and then measure the absorbance value of each at 496 nm. Next, carefully remove as much of the octanol upper phase as possible from each of the test samples and then add 150 microLiters of the lower aqueous buffer phase from each of the 11 test samples to 11 vials of base solution, mix and then measure the absorbance value of each at 496 nm. Plot the absorbance values for both the octanol phase and the buffer phase as a function of pH. The pH at which the two plots cross is the pH of transition, or pT value, for that embedder peptide.

b) Aggregation in Aqueous Buffers

Aggregation studies are carried out the same as above except without the octanol phase. In this case one plots as a function of pH only the absorbance of the buffer phase after centrifugation, and the pH at which the absorbance has dropped to half of the maximum value is taken as the pH of aggregation, or pA value. Typically, for a good embedder peptide the pA value is about 0.3 to 0.4 pH unit below the pT value.

Example 6

Binding Studies with Red Cell Ghosts

Red blood cell ghosts can be used to easily, rapidly, and quantitatively determine the pH at which an embedder peptide will embed into membranes of human cells (the pE value). To begin, place 10 ml of fresh human blood in a 50 ml centrifuge tube, add 40 ml of normal saline (0.15 M NaCl), cap, centrifuge down the red cells, and discard the supernatant. Resuspend the cell pellet in another 45 ml of normal saline and again centrifuge down the red cells and discard the supernatant. Repeat this wash process one more time. To the cell pellet rapidly add 45 ml of distilled water to release the hemoglobin from the red cells. Cap and centrifuge down the red cell ghosts (typically 10,000 rpm for 10 minutes). Carefully draw off the red supernatant and discard, leaving the pink pellet of red cell ghosts. Suspend the pellet of ghosts in 45 ml of normal saline/0.1% sodium azide, centrifuge down the ghosts, discard the supernatant, and resuspend the pellet in 3 ml of normal saline/0.1% sodium azide. This red cell ghost suspension should be kept on ice during the experiment, and may continue to be used for several days if stored at 4 degrees C.

Prepare 1 milliMolar stock solution of fluorescent-tagged embedder, as in Example 5.

Prepare buffers as in Example 5, with the following pH values:
a) pH 5.8
b) pH 6.0
c) pH 6.2
d) pH 6.4
e) pH 6.6
f) pH 6.8
g) pH 7.0
h) pH 7.2

In 1.5 ml plastic centrifuge tubes add: 3 microLiters of stock embedder solution
1000 microLiters of one of the 8 buffer solutions
15 microLiters of red cell ghost suspension -continued For controls prepare:

(no ghosts)  3 microLiters of stock embedder solution
1000 microLiters of pH 6.6 buffer solution
15 microLiters of normal saline (no embedder)  3 microLiters of normal saline
1000 microLiters of pH 6.6 buffer solution
15 microLiters of red cell ghost suspension Cap the tubes, mix well, incubate at 37 degrees C. in waterbath. After the 37 degree incubation, quickly centrifuge in microcentrifuge (10,000 rpm, 10 min).

Carefully (without disturbing the ghost pellet) remove 0.8 ml of each supernatant and add it to 0.2 ml of 1.0 M NaOH, and then measure the absorbance of this initial supernatant at 496 nm. Next, carefully draw off and discard the remaining supernatant from the pellet in each tube, then add to the pellet 0.8 ml of water and 0.2 ml of 1.0 M NaOH to extract embedder peptide from the ghost pellet, mix well, again centrifuge down the ghosts, and then measure the absorbance of this second supernatant (extract of pellet) at 496 nm. Lastly, plot the absorbance values for both the initial supernatants and the second supernatants (extracts of pellets) as a function of pH. The pH at which the two plots cross is the pH of embedding, or pE value, for that embedder peptide.

Example 7

Cell Entry Studies with Cultured Cells

Binding studies with live metabolically active cultured cells are recommended to further confirm the pE values obtained with red cell ghosts. These tests add the important factor of a cytosolic compartment having a pH typically in the range of about 7.2 to 7.5.

Stock solution of embedder composition: To begin, prepare a 2 milliMolar isotonic solution of embedder peptide in its sodium salt form, as follows: weigh out 20 microMoles of fluorescein-tagged embedder peptide in its free acid form (typically about 70 to 100 milligrams). Add 546 milligrams of mannitol, 9.5 milliliters of water, and 0.1 milliliter of 1 Molar aqueous NaOH. Using a pH meter with a microprobe, while stirring slowly add more 1 M aqueous NaOH to effect complete disolution of the embedder composition and raise the pH to about 8.0 (typically requires about an additional 0.1 ml of NaOH solution). Cap and sterilize for 30 minutes at 120 degrees. Alternatively, the embedder solution can be sterilized by passing through a sterile 0.2 micron filter.

Preparation of nine buffered media: Next, prepare 3 portions of Minimum Essential Medium Eagle (MEM) cell culture medium. Each the three portions is buffered using one or the three buffers described in Example 5. Specifically, to one portion add MES buffer to a concentration of 50 milliMole, and then while stirring and monitoring pH, slowly add 1.0 M NaOH to give the desired pH values. When a desired pH is reached, set aside a suitable portion and continue the titration to the next desired pH. For the MES-buffered medium prepare portions at pH 5.8, 6.0, 6.2, and 6.4. Repeat this process with medium buffered with ACES, and take portions at pH 6.6, 6.8, and 7.0. Repeat the process with medium buffered with HEPES, and take portions at pH 7.2 and 7.4. Each portion of these 9 buffered media should then be passed through a 0.2 micron sterile filter into a sterile vial, capped and then stored at 4 degrees C. until use.

Preparation of cultured cells: Seed Hela cells into two 24-well culture plates and allow cells to grow to confluency in 1 ml (each well) of DMEM-F12 media (Catalog # 11330-032, Gibco BRL, Gaithersburg, Md.) containing 5% fetal bovine serum. Wash cells in each well with MEM (without serum), and then wash 9 sets of wells, three wells per set, where each set is washed with one of the nine buffered media prepared above. Next, add to each of three wells in a set 1 ml of that same buffered medium(without serum) to which has been added 10 microLiters of stock embedder solution. Swirl and place in 37 degree C. incubator for 2 hours. After the 2 hour incubation, wash each of the three wells of a set with three 1 ml portions of the same buffered medium (without serum) pre-warmed to 37 degrees C., but lacking the embedder solution.

Observe the washed cells under a fluorescent microscope. Photograph each well of cells first using phase contrast, and then in the fluorescence mode. Lastly, add to each well 0.8 ml of water and 0.2 ml of 1.0 M NaOH to extract embedder component from the cells, swirl for 1 minute, transfer each solution to a 1.5 ml centrifuge tube, centrifuge (10,000 rpm, 10 min) to pellet cell debris, and then use a spectrofluorometer to measure the fluorescence of the supernatant. Note: generally there is too little fluorescence in the samples to get a reliable absorbance reading, and so a fluorescence measurement is typically needed. Lastly, plot the emission values as a function of pH. The pH at which the emission has dropped to half of the maximum value is taken as the pH of embedding, or pE value.

It is recommended that this test be repeated, but with buffered media containing 5% fetal calf serum, but only at pH values of 6.4, 6.6, 6.8, 7.0, 7.2 and 7.4 (going below pH 6.4 can cause precipitation of serum proteins). This study in the presence of serum provides information on embedder activity in those areas of tumors where the capillary walls are sufficiently leaky to allow serum proteins to enter the interstitial space of the tumor.

Where feasible, cell embedding studies, as described above, should also be carried out with embedder compositions containing therapeutic moieties to confirm both that the embedder composition can embed into the membrane of cells and that the selected therapeutic moiety of the embedder composition is effective for directly or indirectly killing the cells in whose membranes the embedder composition has embedded.

Example 8

Studies in Tumor-Bearing Animals

The easiest in vivo test of embedder activity for diagnostic applications is to prepare technetium-labeled diagnostic embedder compositions, such as shown in FIG. 17. Each embedder composition, formulated as in Example 7 and complexed with technetium, is then injected into a tumor-bearing mouse or larger mammal and then that test subject scanned with a gamma scintillation camera periodically over a period of up to about 24 hours to assess the amount of technetium remaining in the body, as well as the ratio in tumor versus in normal tissue.

Said tests should be carried out both as above, and also with pre-treatment to further reduce the pH within acidic areas of tumors, as described in section V part B.

For assessing in vivo embedder activity for therapeutic applications it may be desirable to obtain more precise information with respect to spatial distribution of the embedder composition within the tumor. For this purpose it is recommended that embedder compositions be prepared with structures as in FIG. 17, but wherein the chelator moiety is replaced with a fluorescein or tetraethylrhodamine moiety. The test animal is injected with a composition of this type and, after a suitable period of time for extracellular material to be cleared from the body, the tumor is excised, frozen, thin slices of that tumor taken in a cryostat, and the slices viewed under a fluorescent microscope. Results from such studies can provide useful information regarding the microscopic distribution of embedder composition within the tumor. This level of precision in assessing spatial distribution of the embedder composition can answer key questions such as the following.

a) Is the embedder composition largely limited to areas fairly close to capillaries, and so apparently failing to reach more acidic areas further from the capillaries? This is a possible limitation when the pE of the embedder is too high.

b) Is the embedder composition only labeling areas of the tumor most distant from the capillaries, while failing to embed into the membranes of cells in less acidic areas closer to capillaries? This is a possible limitation when the pE of the embedder is too low.

It is envisioned that answers to such questions will be valuable in guiding the development of an optimal embedder composition or combination of embedder compositions for therapeutic applications.

These more detailed fluorescent microscope-based spatial distribution studies should be carried out both as above, and also with pre-treatment to further reduce the pH within acidic areas of tumors, as described in section V part B.

SCOPE OF THE INVENTION

The above presents a description of the best mode contemplated of carrying out the present invention, and of the manner and process of making and using it, in such full, clear, and exact terms as to enable a person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

What is claimed is:

1. An embedder composition for positioning a moiety onto the surface of cells in acidic areas of a tumor, wherein said embedder composition comprises (a) an embedder peptide which is poly-anionic at pH 7.2 and above, and that converts to a lipophilic form effective to embed into the membranes of cells at a pH below 7.2 that is present in acidic areas of a tumor, said embedder peptide containing (xi) a peptide sequence ranging in length from about 16 to about 50 amino acids, (xii) wherein said peptide sequence contains at least three acid pairs, where said acid pairs except for the acid pair closest to the entry end are selected from the group consisting of EE, ELLE, and ELLLE, wherein 'L' is a lipophilic amino acid selected from the group consisting of leucine, isoleucine, norleucine and methionine, (xiii) each acid of the acid pairs of said peptide sequence except for the acid closest to the entry end is a side chain carboxyl of glutamic acid, (xiv) the acid closest to the entry end is selected from the group consisting of a side chain carboxyl of glutamic acid and another carboxyl-containing side chain effective to form an acid pair with a nearby glutamic acid side chain, (xv) the number of acid side chains in said peptide sequence is less than 45% of the total side chains in said peptide sequence, (xvi) in said peptide sequence the axial center point of one acid pair relative to the axial center point of the adjacent acid pair along the alpha-helical peptide backbone is rotated by a number of degrees selected from the group consisting of 450, 500, 550, 600, and 650 degrees, except for the rotation between an EE acid pair and an ELLE acid pair which is 700 degrees, and the rotation between an EE acid pair and an ELLLE acid pair which is 750 degrees, (xvii) the average of the axial rotations between acid pairs in said peptide sequence is at least 450 degrees, (xviii) at least 90% of the non-acid side chain amino acids of said peptide sequence are lipophilic amino acids (L) selected from the group consisting of leucine, isoleucine, norleucine and methionine, (xix) the entry end of said peptide sequence is predominantly non-ionic at a pH that is present in acidic areas of a tumor, (xx) at least 90% of the amino acids of said peptide sequence are of the same chirality; and, (b) a cargo component which prevents passage across cell membranes, and which contains at least one moiety selected from the group consisting of a diagnostic moiety and a therapeutic moiety.

2. The embedder composition of claim 1 wherein at least 90% of the amino acids of the embedder peptide sequence have D chirality.

3. The embedder composition of claim 1 wherein the cargo component contains at least one diagnostic moiety which is effective for in vivo detection of cells into whose membranes the embedder peptide is embedded.

4. The embedder composition of claim 1 wherein the cargo component includes at least one moiety effective to bind a radioactive element, and which further includes that radioactive element.

5. The embedder composition of claim 4 wherein the radioactive element is technetium 99.

6. The embedder composition of claim 1 wherein the cargo component contains at least one therapeutic moiety which is effective to kill cells into whose membranes the embedder peptide is embedded.

7. The embedder composition of claim 6 wherein the cargo component includes a radioisotope.

8. The embedder composition of claim 6 wherein the cargo component includes a phosphoserine moiety.

9. A composition for positioning a moiety on the surface of cells, wherein said composition comprises
(a) a peptide which includes an amino add sequence motif selected from the group consisting of ELLLELEL-LELELLLE and ELLELELLLELELLEL; "wherein 'L' is a lipophilic amino acid selected from the group consisting of leucine, isoleucine, norleucine and methionine", and,
(b) a moiety which cannot be pulled across a cell membrane by said peptide.

10. The composition of claim 9, which has the structure Moiety-LELLLELELLLELELLLELELLELELLLE(L)n-(NH—CH2—CH(CH3)2), where n is selected from the group consisting of one, two, and three.

11. A method for positioning a moiety on the surface of cells in acidic areas of a tumor in an animal, said method comprising
(a) providing an embedder composition including
an embedder peptide which is poly-anionic at pH 7.2 and above, and that converts to a lipophilic form effective to embed into the membrane of cells at a pH below 7.2 that is present in acidic areas of a tumor, said embedder peptide containing
  (i) a peptide sequence ranging in length from about 16 to about 50 amino acids,
  (ii) wherein said peptide sequence contains at least 3 acid pairs, where said acid pairs except for the acid pair closest to the entry end are selected from the group consisting of EE, ELLE, and ELLLE, "wherein 'L' is a lipophilic amino acid selected from the group consisting of leucine, isoleucine, norleucine and methionine", the group consisting of leucine, isoleucine, norleucine and methionine",
  (iii) each acid of the acid pairs of said peptide sequence except for the acid closest to the entry end is a side chain carboxyl of glutamic acid,
  (iv) the acid closest to the entry end is selected from the group consisting of a side chain carboxyl of glutamic acid and another carboxyl-containing side chain effective to form an acid pair with a nearby glutamic acid side chain,
  (v) the number of acid side chains in the embedder peptide sequence is less than 45% of the total side chains in the embedder peptide sequence,
  (vi) in said peptide sequence the axial center point of one acid pair relative to the axial center point of the adjacent acid pair along the alpha-helical peptide backbone is rotated by a number of degrees selected from the group consisting of 450, 500, 550, 600, and 650 degrees, except for the rotation between an EE acid pair and an ELLE acid pair which is 700 degrees, and the rotation between an EE acid pair and an ELLLE acid pair which is 750 degrees,
  (vii) the average of the axial rotations between acid pairs in said peptide sequence is at least 450 degrees,
  (viii) at least 90% of the non-acid side chain amino acids of said peptide sequence are lipophilic amino acids (L) selected from the group consisting of leucine, isoleucine, norleucine and methionine,
  (ix) the entry end of said peptide sequence is predominantly non-ionic at a pH that is present in acidic areas of a tumor,
  (x) at least 90% of the amino acids of said peptide sequence are of the same chirality, and a cargo component which cannot be pulled across a cell membrane by the embedder peptide, and which contains at least one moiety selected from the group consisting of a diagnostic moiety and a therapeutic moiety, and
(b) introducing said embedder composition into the animal.

12. The method of claim 11 wherein the animal is a human.

13. A method for detecting in a patient tumors which have acidic areas, said method comprising
(a) providing at least one embedder composition of claim 1 wherein the cargo component contains at least one diagnostic moiety,
(b) introducing at least one said composition into the patient,
(c) waiting for a period of time of about from one hour to about twenty-four hours to allow clearance of said composition which has not embedded into membranes of cells, and
(d) scanning the patient with equipment effective to detect the position and amount of said composition remaining in the patient.

14. The method of claim 13 which also includes first treating the patient with a substance effective to temporarily further reduce the pH in acidic areas of tumors.

15. The method of claim 14 where said substance includes glucose.

16. A method for treating tumors in a patient, said method comprising
(a) providing at least one embedder composition of claim 1 wherein the cargo component contains at least one therapeutic moiety, and
(b) introducing at least one said composition into the patient.

17. The method of claim 16 wherein the patient also receives conventional cancer therapy selected from the group consisting of chemotherapy and radiation that is effective to kill fast-dividing cells of tumors.

18. The method of claim 16 which includes first treating the patient with a substance effective to temporarily further reduce the pH in acidic areas of tumors.

19. The method of claim 18 where said substance includes glucose.

20. The method of claim 18 wherein the patient also receives conventional cancer therapy selected from the group consisting of chemotherapy and radiation that is effective to kill fast-dividing cells of tumors.

21. A precursor form of an embedder composition for positioning a moiety onto the surface of cells in acidic areas of a tumor, wherein said precursor form of an embedder composition comprises
(a) an embedder peptide which is poly-anionic at pH 7.2 and above, and that converts to a lipophilic form effective to embed into the membranes of cells at a pH below 7.2 that is present in acidic areas of a tumor, said embedder peptide containing (i) a peptide sequence ranging in length from about 16 to about 50 amino acids, (ii) wherein said peptide sequence contains at least 3 acid pairs, where said acid pairs except for the acid pair closest to the entry end are selected from the group consisting of EE, ELLE, and ELLLE "wherein 'L' is a lipophilic amino acid selected from the group consisting of leucine, isoleucine, norleucine and methionine", (iii) each acid of the acid pairs of said peptide sequence except for the acid closest to the entry end is a side chain carboxyl of glutamic acid, (iv) the acid closest to the entry end is selected from the group consisting of a side chain carboxyl of glutamic acid and another carboxyl-containing side chain effective to form an acid pair with a nearby glutamic acid side chain, (v) the number of acid side chains in said peptide sequence is less than 45% of the total side chains in said peptide sequence, (vi) in said peptide sequence the axial center point of one acid pair relative to the axial center point of the adjacent acid pair along the alpha-helical peptide backbone is rotated by a number of degrees selected from the group consisting of 450, 500, 550, 600, and 650 degrees, except for the rotation between an EE acid pair and an ELLE acid pair which is 700 degrees, and the rotation between an EE acid pair and an ELLLE acid pair which is 750 degrees, (vii) the average of the axial rotations between acid pairs in said peptide sequence is at least 450 degrees, (viii) at least 90% of the non-acid side chain amino acids of said peptide sequence are lipophilic amino acids (L) selected from the group consisting of leucine, isoleucine, norleucine and methionine, (ix) the entry end of said peptide sequence is predominantly non-ionic at a pH that is present in acidic areas of a tumor, (x) at least 90% of the amino acids of said peptide sequence are of the same chirality; and, (b) a precursor to a cargo component, where said precursor is reactive toward a substance such that when said precursor and said substance are contacted they form a cargo component which prevents passage across cell membranes, and which contains at least one moiety selected from the group consisting of a diagnostic moiety and a therapeutic moiety.

22. The composition of claim 21 wherein said precursor to a cargo component contains a chelator moiety effective to bind a radioactive substance.

* * * * *